(12) United States Patent
Oepen et al.

(10) Patent No.: US 8,617,114 B2
(45) Date of Patent: Dec. 31, 2013

(54) DRUG COATED BALLOON CATHETER

(75) Inventors: Randolf von Oepen, Los Altos Hills, CA (US); Travis R. Yribarren, San Mateo, CA (US); Kevin J. Ehrenreich, San Francisco, CA (US); William E. Webler, Jr., San Jose, CA (US); Richard R. Newhauser, Redwood City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 217 days.

(21) Appl. No.: 12/371,430

(22) Filed: Feb. 13, 2009

(65) Prior Publication Data
US 2009/0254063 A1 Oct. 8, 2009

Related U.S. Application Data

(63) Continuation-in-part of application No. 12/171,134, filed on Jul. 10, 2008.

(60) Provisional application No. 60/949,736, filed on Jul. 13, 2007.

(51) Int. Cl.
*A61M 5/178* (2006.01)
*A61M 31/00* (2006.01)
*A61M 29/00* (2006.01)

(52) U.S. Cl.
USPC ............ 604/164.09; 604/103.02; 604/96.01; 604/97.01; 604/164.13

(58) Field of Classification Search
USPC .......... 604/102.01–102.03, 509, 103–103.02, 604/164.09, 164.03, 194, 96.01, 164.13, 604/97.01, 103.03
See application file for complete search history.

(56) References Cited

U.S. PATENT DOCUMENTS

| | | | | |
|---|---|---|---|---|
| 4,243,040 A | * | 1/1981 | Beecher | 606/127 |
| 4,324,262 A | * | 4/1982 | Hall | 600/569 |
| 4,946,440 A | * | 8/1990 | Hall | 604/164.09 |
| 5,102,402 A | * | 4/1992 | Dror et al. | 604/265 |
| 5,304,121 A | | 4/1994 | Sahatjian | |
| 5,534,007 A | * | 7/1996 | St. Germain et al. | 623/1.11 |
| 5,879,499 A | | 3/1999 | Corvi | |
| 6,015,815 A | | 1/2000 | Mollison | |
| 6,139,517 A | | 10/2000 | Macoviak et al. | |
| 6,280,412 B1 | | 8/2001 | Pederson et al. | |
| 6,287,285 B1 | | 9/2001 | Michal et al. | |

(Continued)

FOREIGN PATENT DOCUMENTS

| | | |
|---|---|---|
| EP | 0 359 489 | 3/1990 |
| WO | WO 98/50101 | 11/1998 |
| WO | WO 2009/012163 | 1/2009 |

OTHER PUBLICATIONS

U.S. Appl. No. 12/171,134, Jul. 29, 2011 Final Office Action.

(Continued)

*Primary Examiner* — Emily Schmidt
*Assistant Examiner* — Bradley G Thomas, Jr.
(74) *Attorney, Agent, or Firm* — Baker Botts LLP

(57) ABSTRACT

The present invention relates to balloon catheters for treating a luminal system of a patient. Specifically, the invention relates to catheters having a flexible membrane positioned at a distal portion of the catheter, the flexible membrane retained in a substantially unexposed conformation prior to deployment. Preferably the flexible membrane is capable of delivering a therapeutic agent to a localized environment when deployed to an exposed conformation.

12 Claims, 11 Drawing Sheets

(56) References Cited

U.S. PATENT DOCUMENTS

| | | | |
|---|---|---|---|
| 6,329,386 B1 | 12/2001 | Mollison | |
| 6,495,152 B2 | 12/2002 | Steinbuchel et al. | |
| 6,541,116 B2 | 4/2003 | Michal et al. | |
| 7,744,594 B2* | 6/2010 | Yamazaki et al. | 606/41 |
| 2002/0009535 A1 | 1/2002 | Michal et al. | |
| 2002/0123505 A1 | 9/2002 | Mollison et al. | |
| 2002/0138128 A1 | 9/2002 | Stiger et al. | |
| 2003/0105508 A1 | 6/2003 | Johnson et al. | |
| 2003/0129215 A1 | 7/2003 | Mollison et al. | |
| 2005/0288632 A1 | 12/2005 | Willard | |
| 2006/0058815 A1 | 3/2006 | Mickley et al. | |
| 2006/0149365 A1* | 7/2006 | Fifer et al. | 623/1.46 |
| 2009/0018501 A1 | 1/2009 | Yribarren et al. | |
| 2009/0254063 A1 | 10/2009 | Oepen et al. | |
| 2013/0006220 A1 | 1/2013 | Yribarren et al. | |

OTHER PUBLICATIONS

U.S. Appl. No. 12/171,134, Jul. 26, 2011 Supplemental Response to Non-Final Office Action.

U.S. Appl. No. 12/171,134, May 23, 2011 Response to Non-Final Office Action.

U.S. Appl. No. 12/711,134, Feb. 23, 2011 Non-Final Office Action.

U.S. Appl. No. 12/171,134, filed Jul. 10, 2008.

U.S. Appl. No. 12/171,134, Dec. 12, 2011 Amendment and Request for Continued Examination (RCE).

U.S. Appl. No. 13/616,305, Apr. 30, 2013 Non-Final Office Action.

U.S. Appl. No. 13/616,305, filed Sep. 14, 2012.

Supplementary European Search Report for EP Application No. 08781720, dated May 6, 2013.

* cited by examiner

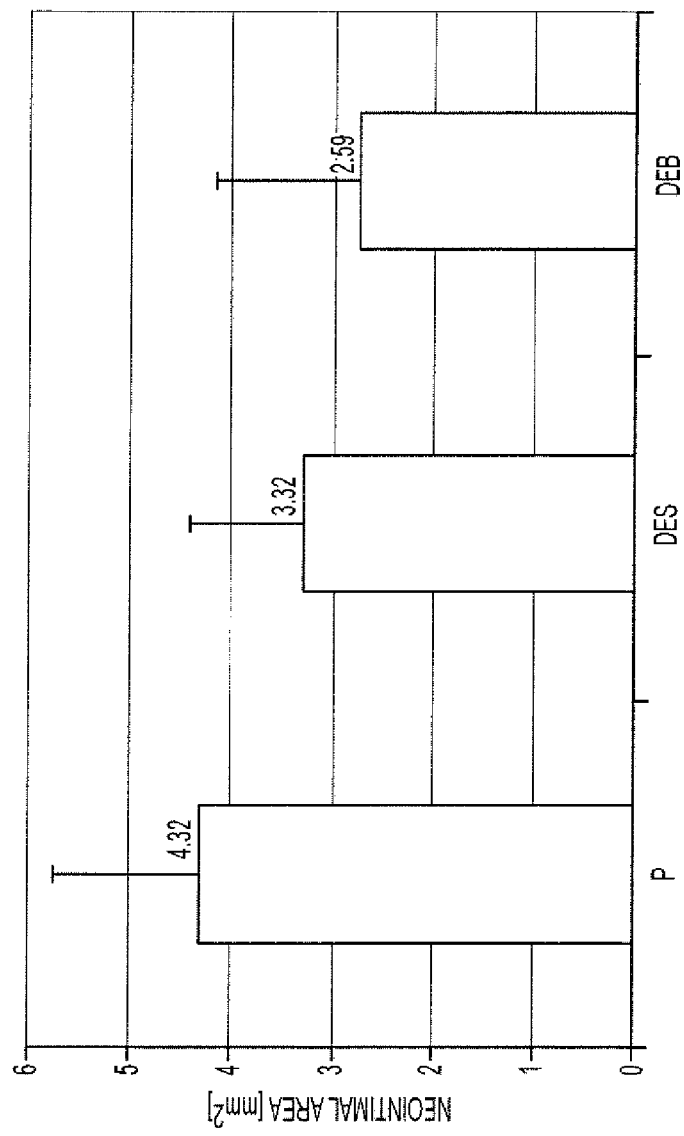

DRUG COATED BALLOON CATHETER

CROSS-REFERENCE TO RELATED APPLICATIONS

This application is a continuation-in-part of U.S. patent application Ser. No. 12/171,134, filed Jul. 10, 2008, which claims priority to U.S. Provisional Application Ser. No. 60/949,736, filed Jul. 13, 2007, each of which is hereby incorporated by reference.

BACKGROUND OF THE INVENTION

1. Field of the Invention

The present invention relates to balloon catheters for treating the luminal systems of a patient. Specifically, the invention relates to catheters having a flexible membrane positioned at a distal portion of the catheter where the flexible membrane is retained in a substantially unexposed conformation prior to deployment. Preferably the flexible membrane is capable of delivering a therapeutic agent to a localized environment when deployed to an exposed conformation.

2. Description of the Related Art

Heart and vascular disease are major problems in the United States and throughout the world. Conditions such as atherosclerosis result in blood vessels becoming blocked or narrowed. If this blockage or narrowing of a vessel occurs in the coronary arteries supporting the heart, which deliver oxygenated blood, this will have significant consequences, since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Such angioplasty techniques typically involve the use of a balloon catheter. Commonly, the balloon catheter is initially advanced over a guidewire so that the balloon is positioned adjacent a stenotic lesion. Once in place, the balloon is then inflated, and the restriction of the vessel is opened.

Typically, balloon catheters are structured such that they have a balloon fastened at least at one end around the exterior of a hollow catheter shaft. The hollow interior of the balloon is in a fluid flow relation with the hollow interior of the shaft. Fluid under pressure can thereby be supplied to the interior of the balloon through the shaft in order to expand the balloon against an obstruction.

Presently catheter balloon materials may be classified as compliant, semi-compliant, or non-compliant balloons. Compliance can be defined as the increase in the balloon diameter above nominal balloon pressure. Generally, non-compliant balloons have less increase in diameter, than semi-compliant balloons, which in turn have less increase in diameter than compliant balloons.

Compliant balloons expand and stretch with increasing pressure within the balloon, and are made from such materials as silicone, thermoplastic elastomers (TPEs), and polyethylene or polyolefin copolymers. Non-compliant balloons, made from such materials as polyethylene terephthalate (PET) or polyamides, remain substantially at a pre-selected diameter as the internal balloon pressure increases beyond that required to fully inflate the balloon.

Compliant balloon materials provide a degree of softness to the balloon which aids its passage through, and expansion within, e.g., blood vessels. Known compliant balloon materials also can display good abrasion and puncture resistance at thicknesses typically used for medical device balloons. In light of the foregoing, it is one object of the present invention to provide a balloon catheter that employs a compliant balloon.

It is an object of the present invention to provide a device that is useful for recovering a balloon predictably and compactly upon deflation to facilitate in vivo movement of the balloon catheter.

In addition to the above-described uses of balloon catheters in PTA, PTCA, and atherectomy, some balloon catheters are made to deliver therapeutic drugs or agents. For example, some balloon catheters deliver a systemic bolus of liquid that includes a drug to a targeted tissue location using an open catheter lumen or channel located at some length along the catheter shaft. Alternatively, the drug can be delivered by coating it on the exterior of the balloon. Unfortunately, when such delivery methods are used to deliver a controlled volume of medication to a desired tissue location, medication may be lost to systemic circulation either because of an inability of the drug to quickly penetrate local tissue, or because the drug coating has been washed away.

In general, liquid formulations containing a drug or agent that are delivered to a targeted tissue location by liquid bolus may not penetrate the tissue sufficiently at the targeted tissue location to result in a significant therapeutic effect, and may be washed away by body fluids. Similarly, drug coated on the surface of a balloon can be washed away due to contact with a circulatory environment, as the circulatory environment matches the environment the drug is designed to target. Such systemic dilution substantially diminishes the effectiveness of the drugs or agents, and increases the likelihood of a greater systemic effect caused by the quantity of drug or agent washed into the bloodstream.

In light of the foregoing, there is a need for an improved balloon catheter capable of delivering therapeutics in a safe and effective manner to targeted tissues within the body. The present invention includes embodiments directed toward solutions that address this unmet need.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied herein and broadly described, the invention includes a balloon catheter with an inner shaft member having a proximal end portion, a distal end portion, and a length therebetween. The balloon catheter also includes an outer shaft member that is movable relative to the inner shaft member and has a proximal end portion, a distal end portion, and a length therebetween. The balloon catheter further includes an annular flow passage disposed between the inner and outer shaft members and a flexible membrane extending between the distal end portion of the inner shaft member and the distal end portion of the outer shaft member. This flexible membrane includes both an inner surface and an outer surface and the inner surface is configured such that it is in fluid communication with the annular flow passage. The inner and outer shaft members of the balloon catheter define a chamber configured to receive the flexible membrane therein. In further accordance with the invention, the flexible membrane can include a therapeutic agent disposed thereon.

In accordance with a further aspect of the invention, the sealed environment of the annular flow passage can be maintained during movement of the outer shaft relative to the inner shaft of the balloon catheter by the inclusion of a bellows component disposed at the proximal end portion of the outer shaft member, or by the inclusion of a dynamic seal disposed between the inner shaft member and the outer shaft member.

In accordance with another aspect of the invention, the flexible membrane of the balloon catheter includes at least one driver segment and a delivery segment, where the driver segment defines at least a portion of a chamber configured to receive the delivery segment. In addition, the driver segment can be constructed of a material having different compliance than that of the delivery segment. Such driver segments can be constructed of materials more or less compliant than the material used to construct the delivery segment. Additionally, the driver segment or segments function to enfold the delivery segment.

In accordance with a further aspect of the invention, the balloon catheter, when in a pre-deployed condition, includes a flexible membrane having spiral formations. Such spiral formations of the flexible membrane can be the result of rotational movement of the outer shaft member relative to the inner shaft member.

The invention also includes a method of treating a luminal system of a patient. The method includes providing a balloon catheter as described herein, positioning the balloon catheter at a desired deployment site, introducing inflation fluid into the annular flow passage, and moving the outer shaft member relative to the inner shaft member to deploy the flexible membrane into an expanded configuration in order to treat the luminal system of the patient. In accordance with a further aspect of the invention, the method of treating a luminal system of a patient includes initial deployment of the flexible membrane to at least partially occlude the luminal system of the patient prior to full expansion of the flexible membrane. In yet another aspect of the invention, the method of treating a luminal system of a patient where the flexible membrane includes a therapeutic agent disposed thereon is provided.

In accordance with a further aspect of the invention, the method of treating a luminal system of a patient includes collapsing the flexible membrane after deployment and treatment of the luminal system of the patient. Such collapse of the flexible membrane can be achieved by withdrawing inflation fluid from the annular flow passage or by movement of the outer shaft member axially or rotatably relative to the inner shaft member.

In accordance with a further aspect of the invention, the method of treating a luminal system of a patient includes repositioning the flexible membrane upon collapse into a chamber configured to receive that membrane, where the chamber is defined by the outer shaft member and the inner shaft member.

The accompanying drawings, which are incorporated in and constitute part of this specification, are included to illustrate and provide a further understanding of the methods and systems of the invention. Together with the description, the drawings serve to explain the principles of the invention.

BRIEF DESCRIPTION OF THE DRAWINGS

These drawings illustrate certain aspects of some of the embodiments of the present invention, and are not intended to be limiting.

FIG. 17 is a graph illustrating results of Neointimal Area [mm] by Histomorphometry of P (TriMaxx Stent on uncoated balloon), DEB (TriMaxx Stent on Zotarolimus coated balloon), and DES (Zomaxx stent on uncoated balloon).

DETAILED DESCRIPTION OF THE PREFERRED EMBODIMENTS

Reference will now be made in detail to the present preferred embodiments of the invention, examples of which are illustrated in the accompanying drawings. The methods and corresponding steps of the invention will be described in conjunction with the detailed description of the system.

The devices and methods presented herein can be used for treating the luminal systems of a patient. The present invention is particularly suited for treatment of the cardiovascular system of a patient, such as delivery of therapeutic agents to specific locations within the patient's circulatory system.

In accordance with the present invention a balloon catheter is provided with an inner shaft member having a proximal end portion, a distal end portion, and a length therebetween. The balloon catheter also includes an outer shaft member that is movable relative to the inner shaft member, and has a proximal end portion, a distal end portion, and a length therebetween. The balloon catheter further includes an annular flow passage disposed between the inner and outer shaft members and a flexible membrane extending between the distal end portion of the inner shaft member and the distal end portion of the outer shaft member. This flexible membrane includes both an inner surface and an outer surface with the inner surface configured such that it is in fluid communication with the annular flow passage.

For purpose of explanation and illustration, and not limitation, exemplary embodiments of a balloon catheter for use in a cardiovascular system and other coronary indications in accordance with the invention are shown in FIGS. 1A-4. Additional features, aspects, and embodiments of a balloon catheter in accordance with the invention are provided in FIGS. 5-14, as will be described. The method of use of the representative embodiments will be described in conjunction with the device.

Figure 1:
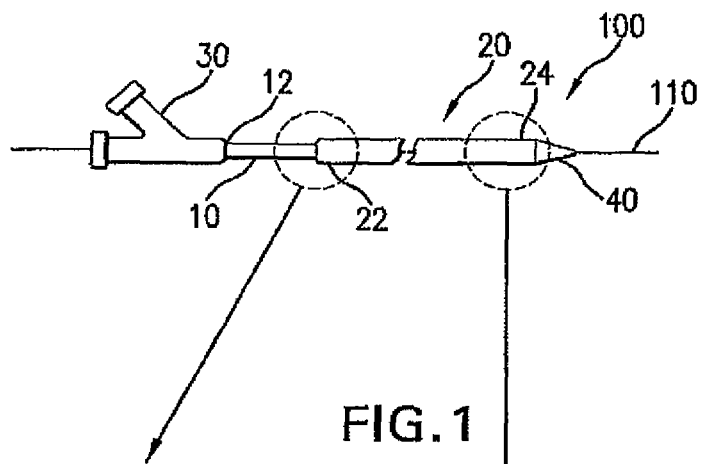
FIG. 1 is a schematic side view of a first representative embodiment of a balloon catheter in accordance with the present invention with a detail cross-sectional view of a flexible membrane at a distal end thereof.
Figure 1A:
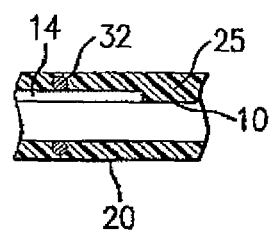
FIG. 1A is an detail view of a dynamic seal near the proximal end of the catheter in accordance with one embodiment of the present invention.
Figure 1A:
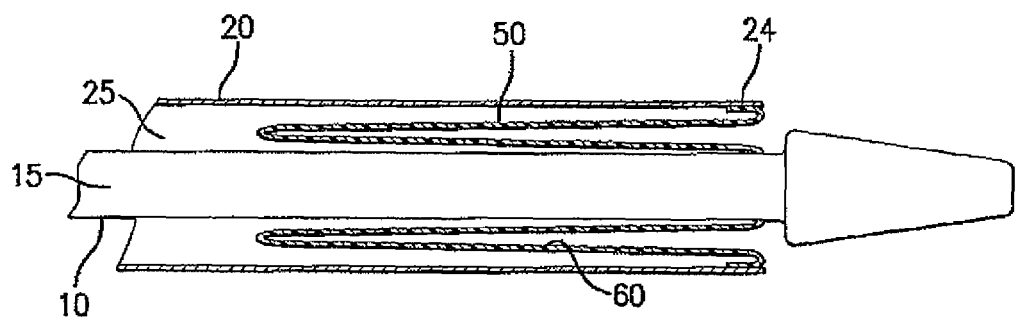
Figure 1B:
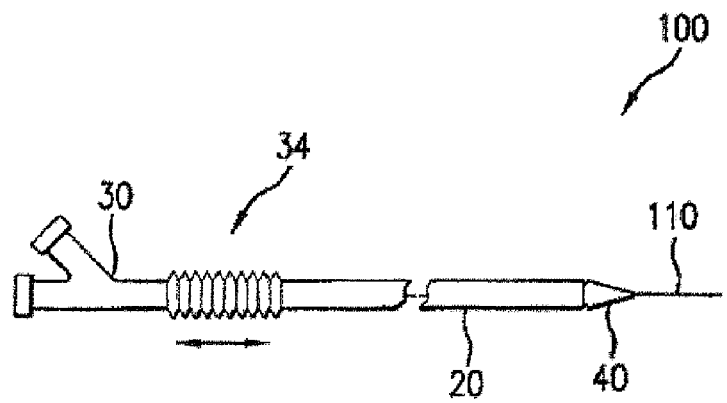
FIG. 1B is a schematic side view of another representative embodiment of a balloon catheter of the present invention, including a bellows component disposed on the outer shaft member.
Figure 1C:
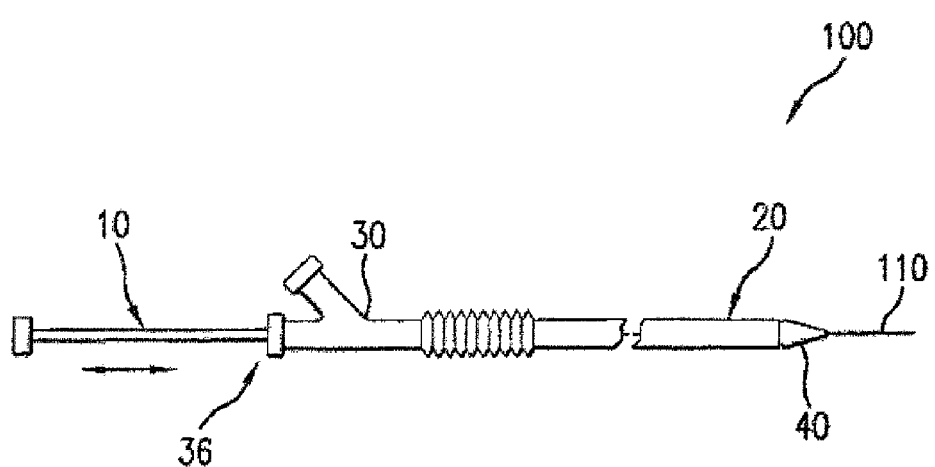
FIG. 1C is a schematic side view of another representative embodiment of a balloon catheter of the present invention, including a dynamic seal integrated into a hub disposed at the proximal end of the catheter.

For purposes of illustration and not limitation, as embodied herein and as depicted in FIGS. 1A-1C, the balloon catheter 100 has an inner shaft member 10 having a proximal end portion 12, a distal end portion 14, and a length therebetween. The balloon catheter 100 also includes an outer shaft member 20 that is movable relative to the inner shaft member 10, and has a proximal end portion 22, a distal end portion 24, and a length therebetween.

The inner and outer shaft members 10, 20 of the balloon catheter 100 can be constructed of any suitable material including but not limited to polymer materials such as nylon, urethane, polyurethane, PEEK, PTFE, PVDF, Kyner, PE, HDPE or polyethylene of various suitable densities. As a further exemplary alternative, the inner and outer shaft members 10, 20 can be constructed of a composite comprising a fabrication of several different materials, such as a co-extrusion of different polymers, or a fiber-reinforced composite material such as fiber reinforced resin materials or braided materials. The inner and outer shaft members 10, 20 can also be constructed of alloy materials, and metallic materials such as stainless steel hypodermic tubing which is available from MicroGroup® Inc., Medway, Md. among other vendors.

It is further contemplated that the inner and outer shaft members 10, 20 can be constructed of any bio-compatible material. As such, the inner and outer shaft members 10, 20 of the balloon catheter 100 can be constructed from the above-identified polymers, combinations or blends of these polymers, whether alone or in combination with other materials, or other bioabsorbable materials.

The inner and outer shaft members 10, 20 can be manufactured using a variety of known techniques such as but not limited to: extrusion, injection molding, air-blowing, stretching, deep drawing, polymerization, cross-linking, dipping from solution, powder depositioning, sintering, electro-spinning, melt spinning, deformation under temperature, stretch blowing, chemical grafting any combination of the above with reinforcement element like metal braids, coils, glass fibers, carbon fibers and other kind of organic or inorganic fibers, liquid crystals, as well as classical machining technologies like milling, drilling, grinding, etc. In the event that metallic elements such as hypotubes, are to be incorporated, various metallic manufacturing techniques can be used, such as but not limited to, machining, tube drawing processes, drilling, milling EDM, other deformation methods, plating sputtering, electrografting, sintering, and depositioning e-polishing, among others. Additionally, the inner and outer shaft members 10, 20 can be constructed from polypropylene or urethane by an extrusion process using an extruder such as that available any of a number of known suppliers, such as Medical Extrusion Technologies, Inc. Murieta, Calif. U.S. Biosynthetic polymer materials can be constructed in a bioreactor according to the process disclosed in U.S. Pat. No. 6,495,152, the entirety of which is hereby incorporated by reference. The materials can be post processed in a number of ways including, for example and not by way of limitation, extrusion, molding, such as by injection or dipping, textile processing such as weaving or braiding, and forming. Forming processes that can be suitable are rolling and welding sheets of material or vacuum forming into tubular shapes, to name only a few examples.

The inner and outer shaft members 10, 20 can be further coated with any of a variety of materials and techniques to enhance performance if desired, including a number suitable coatings and coating techniques subject to patent matters owned by Abbott Laboratories such as U.S. Pat. No. 6,541,116, U.S. Pat. No. 6,287,285, and U.S. Patent Publication No. 2002/0009535, the entireties of which are hereby incorporated by reference. For example, possible coating materials include lubricious materials such as Teflon® available from DuPont De Nemours, Wilmington, Del., U.S., and hydrophobic materials such as silicone lubricant dispersion PN 4097, available from Applied Silicone Corp., Ventura, Calif., U.S., or hydrophilic materials such as hydrogel available from Hydromer, Branchburg, N.J., U.S., or lubricious coatings such as those available from Hydro-Silk of Merritt Island, Fla., U.S.

The inner and outer shaft members 10, 20 can have any suitable cross-sectional shape, including elliptical, polygon, or prismatic, although a circular cross-section generally is preferred. For a coronary balloon, the cross-sectional dimension generally is between about 0.01 millimeters to about 1.50 millimeters, preferably between about 0.10 millimeters and about 1.20 millimeters, most preferably between about 0.25 millimeters and about 1.00 millimeters. It will be appreciated that a balloon used for non-coronary medical applications would have different dimensions, and that this invention can be modified for use in those applications. Furthermore, in the case of a balloon catheter 100 with a "rapid exchange" (RX) guidewire design, the balloon catheter 100 can have an overall length between about 110 centimeters and 400 centimeters, preferably between about 120 centimeters and about 350 centimeters, more preferably the balloon catheter 100 has a length between about 120 centimeters and about 310 centimeters, and most preferably about 135 centimeters. In the case of a balloon catheter 100 with an "over the wire" (OTW) guidewire design, the balloon catheter 100 can have an overall length between about 110 centimeters and 400 centimeters, preferably between about 120 centimeters and about 350 centimeters, more preferably the balloon catheter 100 has a length between about 120 centimeters and about 310 centimeters, and most preferably about 300 centimeters.

In general, the inner shaft member 10 of the instant invention will preferably include an inner lumen 15. In some embodiments, the inner lumen 15 functions as a guidewire lumen. Accordingly, the balloon catheter 100 can be advanced over the guidewire 110 to the desired location. The guidewire lumen 15 can extend along essentially the entire length of the inner shaft member 10 so that the balloon catheter 100 resembles traditional "over-the-wire" catheters, as are well known in the art. Alternatively, the guidewire lumen 15 can extend along only a portion of the inner shaft member 10 so that the balloon catheter 100 resembles "single-operator-exchange" or "rapid-exchange" catheters, as are also well known in the art. Furthermore, "fixed wire" designs, as are well known in the art, may be used in connection with the instant invention as well.

Figure 2:
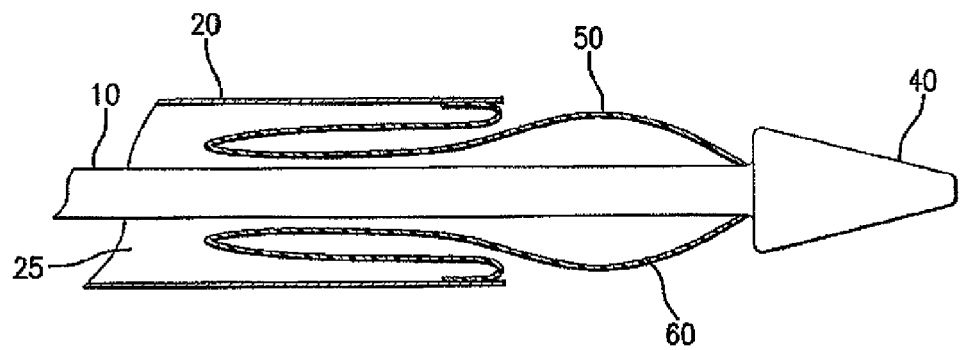
FIG. 2 is a cross sectional view of the distal end of a balloon catheter in accordance with the embodiment of FIG. 1 wherein the flexible membrane is partially deployed.
Figure 3:
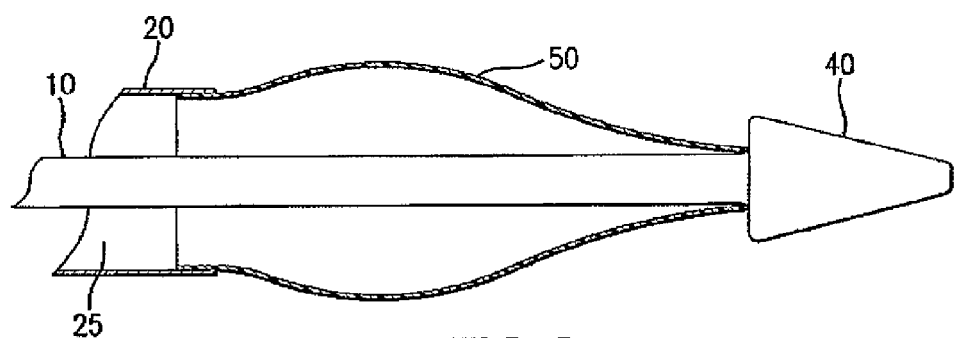
FIG. 3 is a cross sectional view of the distal end of a balloon catheter in accordance with the embodiment of FIG. 1 wherein the flexible membrane is further deployed.
Figure 4:
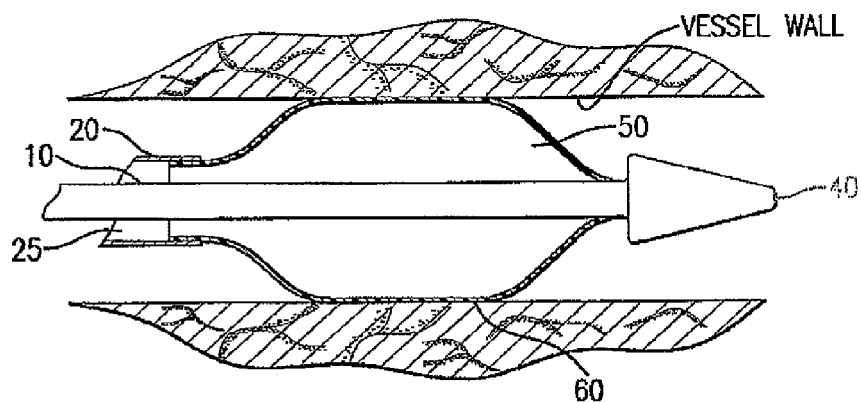
FIG. 4 is a cross sectional view of the distal end of a balloon catheter in accordance with the embodiment of FIG. 1 wherein the flexible membrane is fully deployed.

Referring now to FIGS. 2-4, there is shown a partial cross-sectional side view of the distal end portion of the balloon catheter 100. As shown in FIGS. 2-4, a flexible tip 40 can extend from the distal end portion 14 of the inner shaft member 10. A variety of distal tip configurations are known and used in the art, each generally capable of performing particular functions. In addition, the tip 40 can include a blunt tip or a tip having a pre-formed curve which functions as an atraumatic tip thereby allowing the balloon catheter 100 to be inserted within a patient's vasculature. Such a pre-formed curve ensures that the blunt tip does not pierce the vessel/artery or organ through which the balloon catheter 100 is being advanced. This and other tip designs are well known in the art.

In accordance with another aspect of the invention, the outer shaft member 20 and the inner shaft member 10 define an annular flow passage 25. In certain embodiments, the proximal end portion of the annular flow passage 25 will be either sealably connected directly to an inflation hub unit 30 as shown in FIGS. 1B and 1C, or indirectly to an inflation hub unit 30 via an inflation lumen 14 and dynamic seal 32 as shown in FIGS. 1 and 1A. The sealed environment of the annular flow passage 25 can be maintained during inflation of the flexible membrane and movement of the outer shaft member 20 relative to the inner shaft member 10 due to the presence of a dynamic seal 32, 36 disposed between the outer shaft member 20 and the inner shaft member 10, such as shown in FIGS. 1A and 1C. In certain embodiments this dynamic seal 32 can be located proximal to the inflation hub unit 30, while in other embodiments it can be located distal to the inflation hub unit 30. In accordance with alternative embodiments of the instant invention, the sealed environment of the annular flow passage 25 will be maintained by the presence of a bellows component 34 at the proximal end portion 22 of the outer shaft member 20 as shown in FIG. 1B.

As used herein, the term "flexible membrane," refers to that portion of the balloon catheter 100 capable of undergoing deformation upon the introduction of fluid into the annular flow passage 25. The flexible membrane, referenced in the embodiments herein for purpose of illustration by reference number 50, can be constructed in a manner such that it exhibits noncompliant characteristics, compliant characteristics, or any combination thereof. The flexible membrane 50 can be made of any of a variety of known and suitable materials, as selected for the intended purpose of the balloon catheter 100. Furthermore, if desired, the flexible membrane 50 can be formed of generally inflexible segments joined in a manner to facilitate a generally flexible arrangement that can be deployed as described in detail below. The flexible membrane 50 generally includes a proximal end portion, an intermediate portion, and a distal end portion. The proximal end portion and the distal end portion function as mounting portions to enable the flexible membrane 50 to be mounted to the inner or outer surface of the outer shaft member 20 and the outer surface of the inner shaft member 10 to define the annular flow passage 25 of the balloon catheter 100. With the proximal portion and the distal portion mounted to the inner and outer shaft members 10, 20, the annular flow passage 25 is in sealed fluid communication with the flexible membrane 50.

Figure 11:
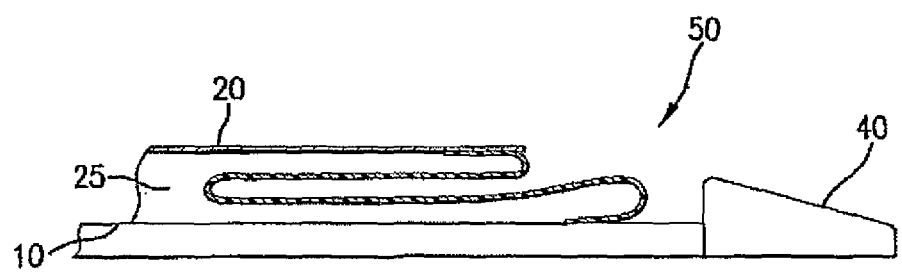
FIG. 11 is a cross sectional view of the distal end of a balloon catheter prior to deployment of the flexible membrane in accordance with another embodiment of the present invention wherein the flexible membrane is attached in an advantageous conformation.
Figure 12:
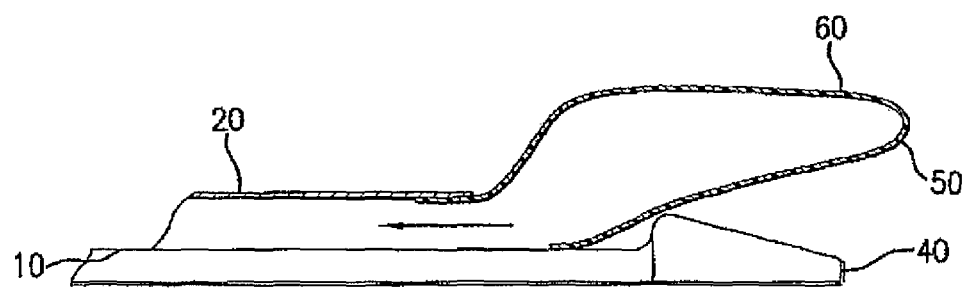
FIG. 12 is a cross sectional view of the distal end of a balloon catheter of FIG. 11 after deployment of the flexible membrane wherein the flexible membrane is attached in an advantageous conformation.

In accordance with particular embodiments of the present invention, the flexible membrane 50 is mounted to the inner and outer shaft members 10, 20 in a configuration that facilitates retraction of the flexible membrane 50 and/or withdrawal of the balloon catheter 100. For example, in a preferred embodiment, the outer surface of the flexible membrane 50 can be mounted to the inner surface of the outer shaft member 20 and the outer surface of the inner shaft member 10 to introduce shoulders as illustrated in FIGS. 11 and 12. Alternative configurations suitable for deployment of the flexible membrane 50 also can be used.

Mounting of the flexible membrane 50 to the inner and outer shaft members 10, 20 can be achieved through use of an adhesive, welded bond (e.g., thermal or chemical weld bond), swaging of metal rings or other known attachment methods or combinations thereof. Optionally, a band, such as a radiopaque marker band, can be utilized to attach the proximal portion and/or the distal portion of the flexible membrane 50 to the inner or outer shaft members 10, 20 or can be used in combination with the above processes. Additional radiopaque markers or marker bands can be secured to the outer surface of the inner or outer shaft members 10, 20 at any position along their length, including within the annular flow passage 25 of the balloon catheter 100.

The marker bands are preferably constructed of materials that facilitate or provide radiopacity. These materials can include, but are not limited to, platinum, alloys of platinum, gold, tungsten, tantalum, or combinations thereof, metals, alloys, plastic, polymer, synthetic material, combinations thereof, or other materials that provide an appropriate radiopaque signature. Alternatively, portions of the balloon catheter 100, including the flexible membrane 50 and/or the inner or outer shaft members 10, 20 can be coated with an appropriate radiopaque material, such as, but not limited to, barium sulphate, bismuth subcarbonate, titanium dioxide, or combinations thereof, to provide radiopacity.

The flexible membrane 50 can be constructed of one or more bio-compatible materials as is known, and if desired, from absorbable biomaterials. One such material is biosynthetic polyester which, advantageously, is tissue compatible and is constructed of component molecules that occur naturally in mammals. The biosynthetic polyester exhibits desirable characteristics for flexible medical devices. For instance, biosynthetic polyesters are very flexible; yet exhibit tensile strengths that are similar to ultrahigh molecular weight polyethylene. These characteristics provide for a flexible membrane 50 that can be tracked through tortuosity easily and has an acceptably high burst pressure. Illustrative biosynthetic polyesters are identified above and include 4-hydroxybutyrate and 3-hydroxybutyrate, as well as poly-L-lactide-co-glycolide, poly-dL-lactide-co-glycolide, polyester amide, chitosan, PBT, and PEG.

As noted above, the balloon catheter 100 can be at least partially loaded with therapeutic agent 60 and such loading will generally occur over some portion of the flexible membrane 50. "Therapeutic agent" as used herein, refers to any compound, mixture of compounds, or composition of matter consisting of a compound, which produces a therapeutic or useful result. The therapeutic agent 60 can be a polymer, a marker, such as a radiopaque dye or particles, or can be a drug, including pharmaceutical and therapeutic agents, or an agent including inorganic or organic drugs without limitation. The agent or drug can be in various forms such as uncharged molecules, components of molecular complexes, pharmacologically acceptable salts such as hydrochloride, hydrobromide, sulfate, laurate, palmitate, phosphate, nitrate, borate, acetate, maleate, tartrate, oleate, and salicylate.

An agent or drug that is water insoluble can be used in a form that is a water-soluble derivative thereof to effectively serve as a solute, and on its release from the device, is converted by enzymes, hydrolyzed by body pH or metabolic processes to a biologically active form. Additionally, the agents or drug formulations can have various known forms such as solutions, dispersions, pastes, particles, granules, emulsions, suspensions and powders. The drug or agent may or may not be mixed with polymer or a liquid as desired.

In an embodiment of the invention, at least one therapeutic agent can be selected from but not limited to anti-proliferative, anti-inflammmatory, antineoplastic, antiplatelet, anticoagulant, anti-fibrin, antithrombotic, antimitotic, antibiotic, antiallergic and antioxidant compounds. Thus, the therapeutic agent can be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, a retroviral vector, an anti-proliferative agent including rapamycin (sirolimus), 40-O-(2-hydroxyethyl)rapamycin (everolimus), 40-O-(3-hydroxypropyl)rapamycin, 40-O-(2-hydroxyethyoxy)ethylrapamycin, 40-O-tetrazolylrapamycin (zotarolimus, ABT-578), paclitaxel, docetaxel, methotrexate, azathioprine, vincristine, vinblastine, fluorouracil, doxorubicin hydrochloride, and mitomycin, an antiplatelet compound, an anticoagulant, an antifibrin, an antithrombins including sodium heparin, a low molecular weight heparin, a heparinoid, hirudin, argatroban, forskolin, vapiprost, prostacyclin, a prostacyclin analogue, dextran, D-phe-pro-arg-chloromethylketone (synthetic antithrombin), dipyridamole, glycoprotein IIb/IIIa platelet membrane receptor antagonist antibody, recombinant hirudin, a thrombin inhibitor including Angiomax ä, a calcium channel blocker including nifedipine, colchicine, a fibroblast growth factor (FGF) antagonist, fish oil (omega 3-fatty acid), a histamine antagonist, lovastatin, a monoclonal antibodie, nitroprusside, a phosphodiesterase inhibitor, a prostaglandin inhibitor, suramin, a serotonin blocker, a steroid, a thioprotease inhibitor, triazolopyrimidine, a nitric oxide or nitric oxide donor, a super oxide dismutase, a super oxide dismutase mimetic, estradiol, an anticancer agent, a dietary supplement including vitamins, an anti-inflammatory agent including aspirin, tacrolimus, dexamethasone and clobetasol, a cytostatic substance including angiopeptin, an angiotensin converting enzyme inhibitor including captopril, cilazapril or lisinopril, an antiallergic agent including permirolast potassium, alpha-interferon, bioactive RGD, and genetically engineered epithelial cells. Other therapeutic agents which are currently available or that can be developed in the future for use with implantable medical devices can likewise be used and all are within the scope of this invention.

Examples of such antithrombotics, anticoagulants, antiplatelet agents, and thrombolytics include sodium heparin, low molecular weight heparins, heparinoids, hirudin, argatroban, forskolin, vapriprost, prostacyclin and prostacylin analogues, dextran, D-phe-pro-arg-chloromethylketone (synthetic antithrombin), dipyridamole, glycoprotein IIb/IIIa (platelet membrane receptor antagonist antibody), recombinant hirudin, and thrombin inhibitors such as Angiomax™, from Biogen, Inc., Cambridge, Mass; and thrombolytic agents, such as urokinase, e.g., Abbokinase™ from Abbott Laboratories Inc., North Chicago, Ill., recombinant urokinase and prourokinase from Abbott Laboratories Inc., tissue plasminogen activator (Alteplase™ from Genentech, South San Francisco, Calif. and tenecteplase (TNK-tPA).

Examples of such cytostatic or antiproliferative agents include rapamycin and its analogs such as everolimus, ABT-578, i.e., 3S,6R,7E,9R,10R,12R,14S,15E,17E,19E,21S,23S, 26R,27R,34aS)-9,10,12,13,14,2-1,22,23,24,25,26,27,32,33, 34,34a-Hexadecahydro-9,27-dihydroxy-3-[(1R)-2-[(-1S, 3R,4R)-3-methoxy-4-tetrazol-1-yl)cyclohexyl]-1-methylethyl]-10,21-dimethoxy-6,8,12,14,20,26-hexamethyl-23,27-epoxy-3H-pyrido[2,1-c][1,4] oxaazacyclohentriacontine-1,5,11,28,29(4H,6H,31H)-pentone; 23,27-Epoxy-3H pyrido[2,1-c][1,4]oxaazacyclohentria-contine-1,5,11,28,29(4H,6H,31H)-pento-ne, which is disclosed in U.S. Pat. No. 6,015,815, U.S. Pat. No. 6,329,386, U.S. Publication 2003/129215, filed on Sep. 6, 2002, and U.S. Publication 2002/123505, filed Sep. 10, 2001, the disclosures of which are each incorporated herein by reference thereto, tacrolimus and pimecrolimus, angiopeptin, angiotensin converting enzyme inhibitors such as captopril, e.g, Capoten® and Capozide® from Bristol-Myers Squibb Co., Stamford, Conn., cilazapril or lisinopril, e.g., Prinivil™ and Prinzide™ from Merck & Co., Inc., Whitehouse Station, N.J.; calcium channel blockers such as nifedipine, amlodipine, cilnidipine, lercanidipine, benidipine, trifluperazine, diltiazem and verapamil, fibroblast growth factor antagonists, fish oil (omega 3-fatty acid), histamine antagonists, lovastatin, e.g. Mevacor™ from Merck & Co., Inc., Whitehouse Station, N.J. In addition, topoisomerase inhibitors such as etoposide and topotecan, as well as antiestrogens such as tamoxifen can be used.

Examples of such anti-inflammatories include colchicine and glucocorticoids such as betamethasone, cortisone, dexamethasone, budesonide, prednisolone, methylprednisolone and hydrocortisone. Non-steroidal anti-inflammatory agents include flurbiprofen, ibuprofen, ketoprofen, fenoprofen, naproxen, diclofenac, diflunisal, acetaminophen, indomethacin, sulindac, etodolac, diclofenac, ketorolac, meclofenamic acid, piroxicam and phenylbutazone.

Examples of such antineoplastics include alkylating agents such as altretamine, bendamucine, carboplatin, carmustine, cisplatin, cyclophosphamide, fotemustine, ifosfamide, lomustine, nimustine, prednimustine, and treosulfin, antimitotics such as vincristine, vinblastine, paclitaxel, e.g., TAXOL® by Bristol-Myers Squibb Co., Stamford, Conn., docetaxel, e.g., Taxotere™ from Aventis S.A., Frankfurt, Germany, antimetabolites such as methotrexate, mercaptopurine, pentostatin, trimetrexate, gemcitabine, azathioprine, and fluorouracil, and antibiotics such as doxorubicin hydrochloride, e.g., Adriamycin™ from Pharmacia & Upjohn, Peapack, N.J., and mitomycin, e.g., Mutamycin™ from Bristol-Myers Squibb Co., Stamford, Conn., agents that promote endothelial cell recovery such as estradiol.

Other agents and materials could conceivably be delivered into a patient anatomy in accordance with the present invention. For example, angiogenetic factors could be delivered. This includes growth factors such as isoforms of vasoendothelial growth factor (VEGF), fibroblast growth factor (FGF, e.g. beta-FGF), Del 1, hypoxia inducing factor (HIF 1-alpha), monocyte chemoattractant protein (MCP-1), nicotine, platelet derived growth factor (PDGF), insulin-like growth factor (HGF), estrogens, follistatin, proliferin, prostaglandin E1 and E2, tumor necrosis factor (TNF-alpha), interleukin 8 (Il-8), hematopoietic growth factors, erythropoietin, granulocyte-colony stimulating factors (G-CSF) and platelet-derived endothelial growth factor (PD-ECGF). In some embodiments, angiogenesis promoting factors include, but are not intended to be limited to, peptides, such as PR39, PR11 and angiogenin, small molecules, such as PHD inhibitors, or other agents, such as eNOS enhancers.

While the foregoing therapeutic agents are known for their preventive and treatment properties, the substances or agents are provided by way of example and are not meant to be limiting. Further, other therapeutic agents that are currently available or may be developed are equally applicable for use with the present invention.

If desired or necessary, the therapeutic agent can include a binder to carry, load, or allow sustained release of an agent, such as but not limited to a suitable polymer or similar carrier. The term "polymer" is intended to include a product of a polymerization reaction inclusive of homopolymers, copolymers, terpolymers, etc., whether natural or synthetic, including random, alternating, block, graft, branched, cross-linked, blends, compositions of blends and variations thereof. The polymer can be in true solution, saturated, or suspended as particles or supersaturated in the therapeutic agent. The polymer can be biocompatible, biosolvable, biostable, or biodegradable.

For purpose of illustration and not limitation, the polymeric material can include phosphorylcholine linked macromolecules, such as a macromolecule containing pendant phosphorylcholine groups such as poly(MPCw:LMAx:HPMAy:TSMAz), where MPC is 2-methacryoyloxyethylphosphorylcholine, LMA is lauryl methacrylate, HPMA is hydroxypropyl methacrylate and TSMA is trimethoxysilylpropyl methacrylate, and w, x, y, and z are molar ratios of the monomers used in the feed. These values are typically 23, 47, 25, and 5, respectively, but they are not necessarily the ratios that exist in the finished polymer. The polymer is herein referred to generally as "PC polymer."

The therapeutic agent can include a liquid. The liquid can be any single solvent or a combination of solvents. For purpose of illustration and not limitation, examples of suitable solvents include water, aliphatic hydrocarbons, aromatic hydrocarbons, alcohols, ketones, dimethyl sulfoxide, tetrahydrofuran, dihydrofuran, dimethylacetamide, acetates, and combinations thereof. Preferably, the solvent is ethanol. More preferably, the solvent is isobutanol. Additionally, in another aspect of the invention, multiple therapeutic agents are dissolved or dispersed in the same solvent. For purpose of illustration and not for limitation, dexamethasone, estradiol, and paclitaxel are dissolved in isobutanol. Alternatively, dexamethasone, estradiol, and paclitaxel are dissolved in ethanol. In yet another example, dexamethasone, estradiol, and ABT-578, i.e., the rapamycin analog, 3S,6R,7E,9R,10R,12R,14S,15E,17E,-19E,21S,23-S,26R,27R,34aS)9,10,12,13,14,21,22,23,24,25,26,27,32,33,34,34a-Hexadecahydro-9,27-dihydroxy-3-[(1R)-2-[(1S,3R,4R)-3-methoxy-4-tetrazol-1-yl)cyclohexyl]-1-methylethyl]-10,21-dimethoxy-6,8,12,14,20,26-hexamethyl-2-3,27-epoxy-3H-pyrido[2,1-c][1,4] oxaazacyclohentriacontine-1,5,11,28,29(4H,-6H,31H)-pentone; 23,27-Epoxy-3H-pyrido[2,1-c][1,4] oxaazacyclohentriacontin-e-1,5,11,28,29(4H,6H,31H)-pentone, are dissolved together in one solvent. Preferably, the solvent is ethanol. More preferably, the solvent is isobutanol.

Additionally, the therapeutic agent includes any of the aforementioned drugs, agents, polymers, and liquids either alone or in combination.

Such therapeutic agents can be applied to the flexible membrane, preferably to the outer surface of the flexible membrane using any of a variety of known techniques suitable for the intended application, thus allowing the presentation of the therapeutic agent to the external environment upon inflation. For example, a variety of techniques to apply a drug to a surface are discussed in various patent applications owned by Abbott Laboratories. The therapeutic agent is employed to induce a therapeutic effect on the tissue at the targeted location in the patient. The inclusion of the therapeutic agent creates the opportunity to provide a medical or therapeutic effect for tissue that makes contact with the flexible membrane. The therapeutic effect can be varied by the particular therapeutic agent loaded onto the balloon catheter. In addition, the therapeutic agent will transfer from the balloon catheter to the targeted tissue location of the patient upon substantive contact with the flexible membrane, and will generally remain at or on the targeted tissue location to penetrate the tissue.

In addition to the therapeutic agent, the balloon catheter may be at least partially loaded with a salt or sugar compound. During expansion of the flexible membrane the salt or sugar compound can be delivered to the target tissue prior to, or concurrently with, the therapeutic agent. Upon delivery to the target tissue, the compound will recruit fluid from the tissue cells. The recruitment of fluid increases the size of the gaps that exist between cells, thereby creating channels for migration of the therapeutic agent. By making the path of the therapeutic agent easier, it will be able to penetrate the target tissue to a greater depth. In this way, a greater volume of therapeutic agent can be delivered in order to provide the intended therapeutic effect.

In accordance with another aspect of the invention, the therapeutic agent will generally be formulated to coat the outer surface of the flexible membrane or be physically positioned in a manner such that an efficacious amount of the therapeutic agent does not wash away with bodily fluid passing by the balloon catheter. Techniques for making such a formulation are well known in the art and include, for example, overlaying a dissolvable film on the coating that allows for the slow release of the agent coated by such a film by including within the coating components that inhibit transfer of the therapeutic coating until heated or expanded. Alternatively, as described above, the agent can be incorporated into a hydrogel that inhibits loss of the agent due to the presence of bodily fluids prior to deployment of the flexible membrane.

In accordance with alternative aspects of the invention, the therapeutic agent 60 can be physically positioned in a manner such that an efficacious amount of the therapeutic agent 60 is not lost due to the presence of bodily fluid contacting the balloon catheter 100. Techniques for physically positioning therapeutic agents 60 on the flexible membrane 50 are well known in the art. Such techniques include, but are not limited to, the positioning of the therapeutic agent 60 within channels or pores on the flexible membrane 50 such that, when in an unexpanded configuration, the channels are inaccessible to the external environment but upon expansion the channels or pores widen and the therapeutic agent 60 is exposed to the external environment. In alternative embodiments of the present invention, the therapeutic agent 60 is contained within microcapsules attached to the flexible membrane 50 and the therapeutic agent 60 is released from the microcapsules by expansion of the flexible membrane 50.

In accordance with another aspect of the present invention, further loss of therapeutic agent 60 by the presence of bodily fluids passing by the balloon catheter 100 is inhibited by rolling the flexible membrane 50 over itself in a generally axial direction, as illustrated in FIG. 2. In such an embodiment, the rolled configuration will isolate the flexible membrane 50 from contact with the bloodstream during device delivery by maintaining the flexible membrane 50 within a chamber defined by the outer shaft member 20 and the inner shaft member 10.

Once the balloon catheter 100 is properly placed within a patient's vasculature, the flexible membrane 50 can be unrolled or otherwise deployed by the introduction of inflation fluid into the annular flow passage 25 and retraction of the distal end 24 of the outer shaft member 20 in a proximal direction relative to the inner shaft member 10. Such retraction can be accomplished while maintaining the annular flow passage 25 by the presence of a dynamic seal 32 between the inner and outer shaft members 10, 20 as illustrated in FIG. 1A, by the presence of a bellows component 34 disposed along the outer shaft member 20 as illustrated in FIG. 1B, or by the presence of a dynamic seal 36 between the inner shaft member 10 and inflation hub unit 30 located at the proximal end 22 of the outer shaft member 20 as illustrated in FIG. 1C. Upon retraction of the outer shaft member 20, the outer surface of the flexible membrane 50 will become partially exposed to the surrounding environment. This partial exposure is illustrated in FIG. 2. Full retraction of the outer shaft member 20 will fully expose the outer surface of the flexible membrane 50 as illustrated in FIG. 3.

Upon retraction, or concurrent therewith, fluid can be communicated through the annular flow passage 25 to inflate and expand the flexible membrane 50 such that the distal surface of the flexible membrane 50 comes in contact with the vessel wall. Expansion of the flexible membrane 50 in response to the introduction of fluid into the annular flow passage 25 is illustrated in FIG. 4. In certain embodiments, the introduction of fluid during retraction of the outer shaft member 20 will be sufficient to induce occlusion of the target vessel by a partially expanded flexible membrane 50, after which complete expansion and treatment can occur.

Figure 5:
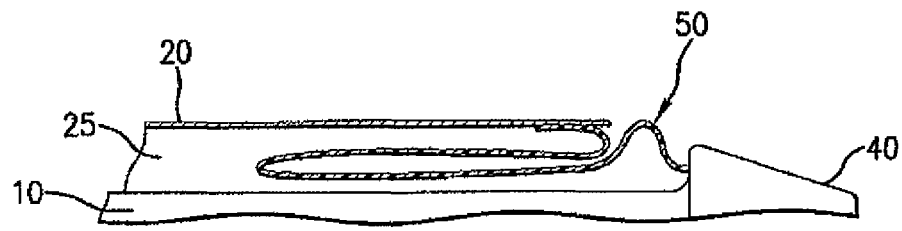
FIG. 5 is a cross sectional view of the distal end of a balloon catheter in accordance with an alternative embodiment of the present invention wherein the flexible membrane is partially deployed.
Figure 6:
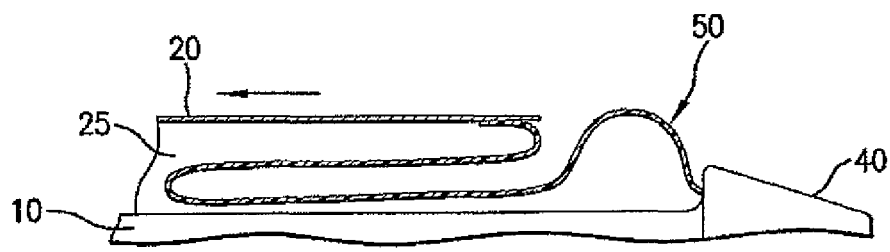
FIG. 6 is a cross sectional view of the distal end of a balloon catheter in accordance with the embodiment of FIG. 5 wherein the flexible membrane is further deployed.
Figure 7:
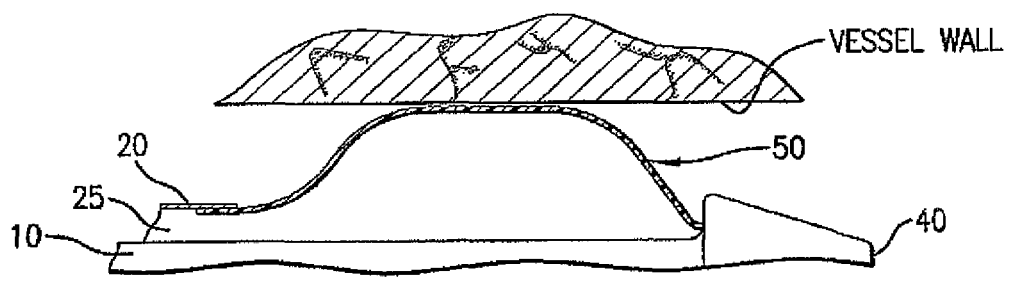
FIG. 7 is a cross sectional view of the distal end of a balloon catheter in accordance with the embodiment of FIG. 5 wherein the flexible membrane is fully deployed.

In an alternative embodiment, the introduction of fluid into the annular flow passage 25 is sufficient in itself to drive the retraction of the outer shaft member 20 relative to the inner shaft member 10, and will lead to inflation of the flexible membrane 50. Such an embodiment is illustrated in FIGS. 5-7, where the flexible membrane 50 preferentially expands in the unconstrained direction and the expansion will cause the flexible membrane 50 to place a proximal load on the outer shaft member 20. As will be appreciated by one of skill in the art, a wide variety of combinations of retraction and introduction of fluid into the annular flow passage 25 fall within the scope of the instant invention and will affect retraction of the outer shaft member 20 and inflation of the flexible membrane 50.

Figure 13A:
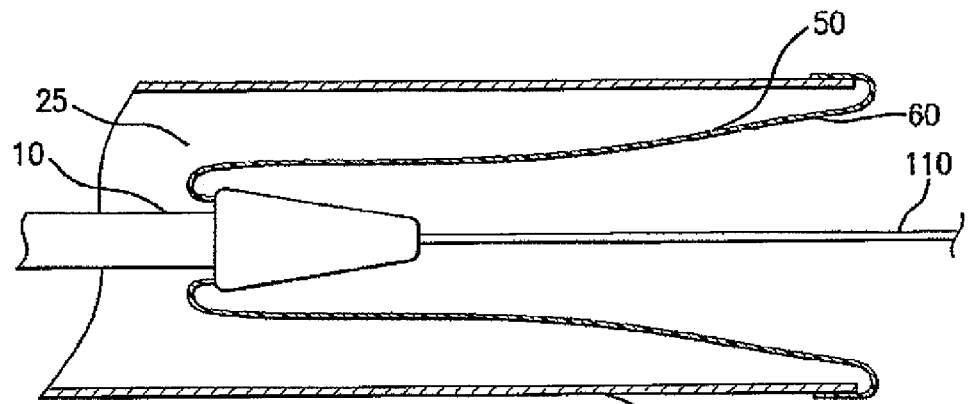
FIG. 13A is a cross sectional view of the distal end of a balloon catheter in accordance with another embodiment of the present invention prior to deployment of the flexible membrane.
Figure 13B:
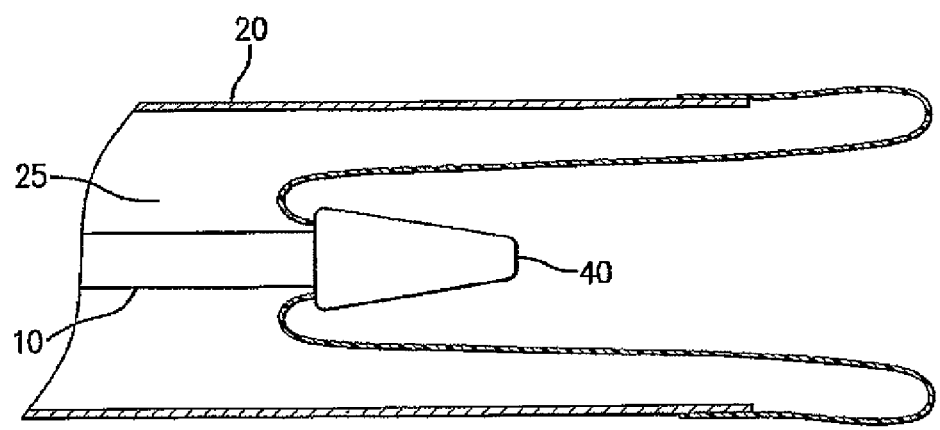
FIG. 13B is a cross sectional view of the distal end of a balloon catheter in accordance with the embodiment of FIG. 13A in the process of deployment of the flexible membrane.
Figure 13C:
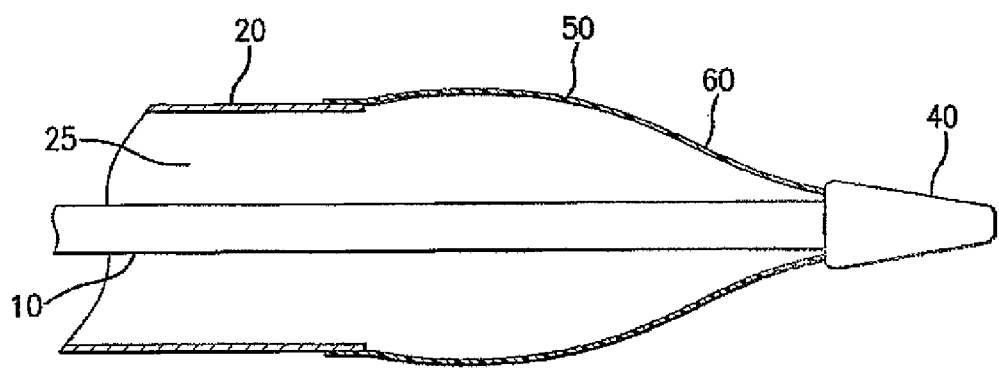
FIG. 13C is a cross sectional view of the distal end of a balloon catheter in accordance with the embodiment of FIG. 13A after deployment of the flexible membrane.

In another embodiment, the balloon catheter 100 has a flexible membrane 50 generally contained within the annular flow passage 25 prior to deployment, such that the flexible membrane 50 is deployed distally by unraveling in a distal direction. As illustrated in FIG. 13A, as fluid is introduced through the annular flow passage 25, the flexible membrane 50 becomes pressurized and is driven forward within the passage. This forward progression results in an unraveling of the flexible membrane 50 as illustrated in FIG. 13B. Once the flexible membrane 50 is fully exposed, as illustrated in FIG. 13C, it will expand against the vessel wall.

In order to prevent loss of the therapeutic agent 60 into the blood stream after deployment, it can be desirable to retrieve the flexible membrane 50 within the annular flow passage 25 defined by the inner and outer shaft members 10, 20. Retrieval can be accomplished by pulling or applying a tensile load on the outer shaft member 20 as shown in FIG. 1C. For example, in one embodiment of the instant invention, such retrieval is accomplished using the proximal end portion 12 of the inner shaft member 10 as a retrieval element. By placing a tensile load on the inner shaft member 10, the distal end 14 of the inner shaft member 10 will cause the flexible membrane 50 to roll back into the annular flow passage 25, where the flexible membrane 50 is protected from the flow of bodily fluid. Such a process of retrieval is illustrated in FIG. 12.

In an alternative embodiment, if the proximal end portion 12 of the inner shaft member 10 is not accessible, it is possible to provide a retrieval element that is not integral to the inner lumen 15 of the inner shaft member 10. For example, this can be accomplished by attaching an element that is associated with the inner shaft member 10 and which can apply a compressive load to the inner shaft member 10 over a portion of length proximal to the point of attachment. Examples of such elements include: sutures, wires, tendons, and rods, all of which can be connected at the distal end of the inner shaft member. Application of a tensile load to the element would transmit a compressive load to the inner shaft member 10, which would thereby cause the flexible membrane 50 to retract within the annular flow passage 25.

The retraction of the flexible membrane 50 can be aided by configuring the proximal and distal ends of the flexible membrane 50 as shown in FIG. 11. When configured in this fashion, when the inner shaft member 10 is compressed in order to retrieve the flexible membrane 50, the distal end of the flexible membrane 50 is curved or provided with a shape memory in a way that makes it preferentially retract into the annular flow passage 25 without becoming bunched up or folded in a way that impedes retrieval.

Figure 8:
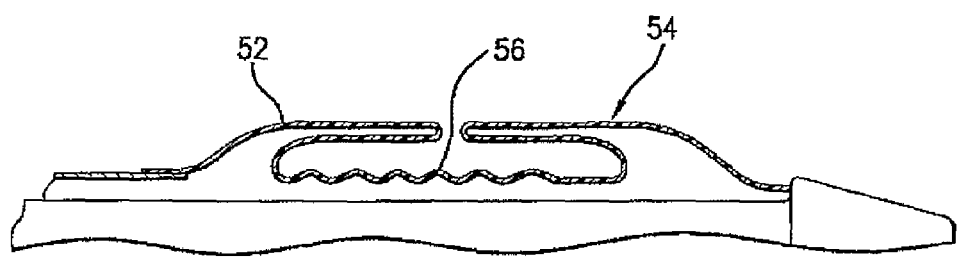
FIG. 8 is a cross sectional view of the distal end of a balloon catheter prior to deployment of the flexible membrane in accordance with another embodiment of the present invention.

In an alternative embodiment, loss of the therapeutic agent 60 by the presence of bodily fluids passing by the balloon catheter 100 can be inhibited by including a flexible membrane 50 having a segmented configuration. As illustrated in FIG. 8, such embodiments can include where the flexible membrane 50 consists of three segments: the proximal driver 52, the distal driver 54, and the intermediate delivery segment 56, however, additional embodiments having fewer or more segments are also specifically contemplated as within the scope of the instant invention. In one exemplary embodiment, proximal and distal driver segments 52, 54 are configured such that the intermediate delivery segment 56 is protected from the surrounding environment, and only the intermediate delivery segment 56 of the flexible membrane is coated with therapeutic agent 60. In certain embodiments it can be preferable to have the intermediate delivery segment 56 composed of a more or less flexible material than the proximal and distal driver segments 52, 54.

Figure 9:
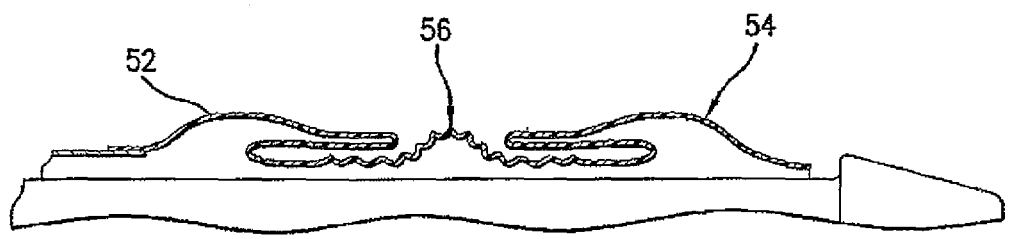
FIG. 9 is a cross sectional view of the distal end of a balloon catheter in accordance with the embodiment of FIG. 8 wherein the flexible membrane is partially deployed.
Figure 10:
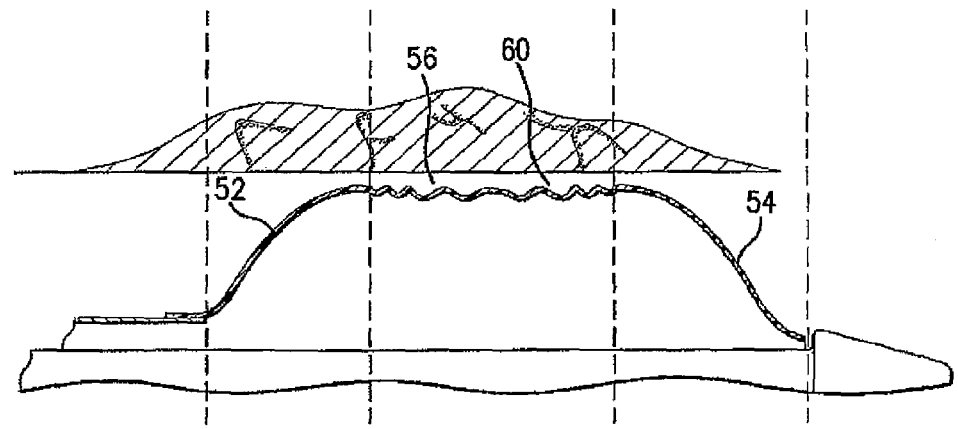
FIG. 10 is a cross sectional view of the distal end of a balloon catheter in accordance with the embodiment of FIG. 8 wherein the flexible membrane is fully deployed.

When fluid is introduced into the annular fluid passage 25, it causes the proximal and distal driver segments 52, 54 to expand and forces them away from each other. This separation can be aided by the axial displacement of the inner and outer shaft members 10, 20 as discussed above, and can be the result of the proximal and distal driver segments 52, 54 and intermediate delivery segment 56 having different compliance. Such separation is illustrated in FIG. 9.

As the proximal and distal driver segments 52, 54 separate, they expose the intermediate delivery segment 56 to the surrounding environment. The unconstrained intermediate delivery segment 56 is then able to expand toward the vessel wall. Upon further inflation, the proximal and distal driver segments 52, 54 and the intermediate delivery segment 56 become fully expanded, bringing the therapeutically coated surface of the intermediate delivery segment 56 in contact with the vessel wall.

In an additional embodiment, the proximal and/or distal driver segments 52, 54 can be designed to preferentially expand to occlude the vessel in one or more locations, thereby preventing bodily fluids from contacting the intermediate delivery segment 56 prior to full inflation of that segment. In one such embodiment the proximal driver 52 can expand first, thereby occluding the proximal end of the vessel and preventing the flow of bodily fluid from contacting the intermediate delivery segment 56 during deployment of the device.

In order to prevent loss of the therapeutic agent 60 into the blood stream after deployment of the segmented flexible membrane 50, it may be desirable to form the proximal and distal driver segments 52, 54 such that they preferentially collapse only after the intermediate delivery segment 56 has collapsed and such that they return to their pre-deployment configuration.

Figure 14:
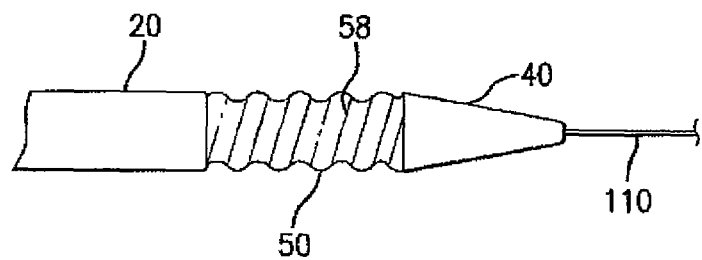
FIG. 14 is a schematic side view of another representative embodiment of a balloon catheter of the present invention wherein the flexible membrane is arranged in a twisted conformation prior to deployment.

In an alternative embodiment, as shown in FIG. 14, loss of the therapeutic agent 60 due to the presence of bodily fluids contacting the balloon catheter 100 can be inhibited by the introduction of spiral formations 58 along the flexible membrane 50. These spiral formations 58 can be introduced by configuring the inner and outer shaft members 10, 20 such that they are rotatably movable with respect to each other. As the flexible membrane 50 is associated with both the inner and outer shaft members 10, 20, the rotation of the shaft members relative to each other will result in a series of spiral formations 58 in the surface of flexible membrane 50, rendering portions of the flexible membrane 50 inaccessible to the external environment and the passing bodily fluids. As such portions are not exposed to the surrounding environment; any therapeutic agent 60 disposed therein would be protected from the blood stream. Upon proper positioning of the balloon catheter 100, the inner and outer shaft members 10, 20 can be rotated in the reverse direction to remove the spiral formations 58 and the flexible membrane 50 can be inflated to effect transfer of the therapeutic agent 60 to the location to be treated.

In accordance with another aspect of the instant invention, loss of the therapeutic agent 60 into the blood stream after deployment of a flexible membrane 50 that has had its spiral formations 58 removed, it would be possible to reintroduce the spiral formations 58 upon collapse of the flexible membrane 50 by rotating the inner and outer shaft members 10, 12 relative to each other. Such reintroduction would effectively prevent the therapeutic agent 60 disposed between the spiral formations 58 from contacting the blood stream during withdrawal or repositioning of the balloon catheter 100.

It will be appreciated, in light of the embodiments described above, that the invention describes a balloon catheter that can be used in a "universal" fashion. In particular, depending upon the length of flexible membrane deployed, the balloon catheter can be used to treat a variety of disease lengths or treatment sites. The operator can control the length of deployment through relative motion of the catheter shaft members such as previously described. Such a system is advantageous not only as it will allow users to stock a single length, but can also reduce the need for the user to swap out devices when a longer or shorter flexible membrane is needed than was initially introduced into the patient.

In accordance with another aspect of the invention and as previously described in conjunction with certain aspects of the invention, a method of treating a luminal system of a patient is provided. The method includes providing a balloon catheter as described herein, positioning the balloon catheter at a desired deployment site, introducing inflation fluid into the annular flow passage and moving the outer shaft member relative to the inner shaft member to deploy the flexible membrane into an expanded configuration in order to treat the luminal system of the patient. As pointed out above, the balloon catheter can take a number of different configurations and the methods of the instant invention envision the use of any such configurations as within their scope.

In accordance with additional aspects of the methods of the instant invention, the balloon catheter includes properties that facilitate its collapse and withdrawal. For example, and not by way of limitation, the methods of the instant invention include the withdrawal of inflation fluid from the annular flow passage and movement of the inner and outer shaft members relative to each other to effect the collapse of the flexible membrane. In one such embodiment, the method includes axially moving the distal end portion of the outer shaft member beyond the distal end portion of the inner shaft member such that the flexible membrane is rendered taut and less likely to catch on luminal structures as the balloon catheter is withdrawn from the patient. In an alternative embodiment, the distal end portion of the inner shaft member is moved axially relative to the outer shaft member such that the distal end portion of the inner shaft member extends beyond the distal end portion of the outer shaft member and the flexible membrane is also rendered taut and less likely to catch on luminal structures as the balloon catheter is withdrawn from the patient. In further embodiments, the methods of the present invention make use of other structures of the balloon catheter described above, such as the chamber configured to receive the flexible membrane defined by the inner and outer shaft members, to facilitate collapse of the flexible membrane and withdrawal of the balloon catheter. Methods of using such structures within the scope of the invention, such as the examples provided herein, would be readily apparent to one of skill in the art.

COMPARATIVE STUDIES

This study compared the effects of Zotarolimus coated angioplasty balloons and Zotarolimus coated stents on the reduction of formation of neointima commonly associated with restenosis. Also evaluated was the influence of Zotarolimus delivered to one coronary artery from a balloon or stent to neotintimal hyperplasia in a separate coronary artery implanted with a bare metal stent. The results of this study indicate the delivery of beneficial agent directly from an angioplasty balloon is an attractive alternative to a drug eluting stent.

STUDY DESIGN/METHODS

A. Animals

Domestic *Sus Scrofa* male, castrated adolescent pigs weighing between 25 to 30 kg were used in these studies. Pigs were acquired from V.B. Zucht und Mast GmbH, Dorfstraβe 12, 39307 Klein Demsin, Germany. During a ten day (minimum) quarantine period and for four additional days, pigs selected from the animal population were given a corn-based high-fiber feed and unfiltered tap water was provided ad libitum. Samples of the water were analyzed for total dissolved solids, harness, specified microbiological content and selected environmental contaminants. No known contaminants were identified which would be expected to interfere with the study. The animals were held in quarantine for a minimum of ten days to ensure the health of each animal before the initiation of the study.

B. Interventional Procedure and Surgical Preparation

The pigs were pre-sedated by intramuscular injection of ketamine and xylazine. A venous access was provided. After sedation, the animals were intubated and maintained in anesthesia with intravenous 3 to 10 ml Propofol (Recofol® 1% (Curamed Pharma GmbH, Germany)). The pigs were intubated (Endonorm 6.5 F, Rusch GmbH, Germany) and ventilation was started using a mixture of 30 vol. % of pure oxygen, 70 vol % $N_2O$ and 1-2 vol % of Isofluran (Isofluran Curamed®, Curamed Pharma GmbH, Germany). After induction of anesthesia, an incision was made in the neck to expose the carotid artery. An arterial sheath was introduced and advanced into the artery. For the interventional procedure, the animals received 5,000 IU of heparin, 250 mg aspirin intravenously (Aspisol®, Bayer AG, Germany), and intracoronary nitroglycerin.

In each of forty-two pigs, one TriMaxx® stent (P) mounted on a bare angioplasty balloon was implanted in a randomly selected artery, i.e., left anterior descending coronary artery (LAD) or left circumflex coronary artery (CX). The remaining coronary vessel was randomly assigned to receive either: (a) a second TriMaxx® stent on a bare balloon (P), (b) a TriMaxx® stent on a drug-eluting balloon (DEB), or (c) a ZoMaxx® drug eluting stent on a bare balloon (DES). Thus, one set of fourteen pigs received two TriMaxx® stents mounted on bare angioplasty balloons in LAD and CX (P-P), a second set of fourteen pigs received one TriMaxx® stent mounted on a bare angioplasty balloon in one coronary artery and a TriMaxx® stent on a drug eluting balloon in the other artery (P-DEB), and a third set of fourteen pigs received a TriMaxx® stent mounted on a bare angioplasty balloon in one artery and a ZoMaxx® drug eluting stent on a bare angioplasty balloon in the other coronary arty (P-DES).

The placebo control was a TriMaxx® Coronary Stent coated with phosphorylcholine (PC) mounted on a PTCA catheter. The drug eluting stent was a ZoMaxx® Coronary Stent coated with PC and Zotarolimus premounted on a PTCA catheter and the drug eluting balloon was an angioplasty balloon coated with Zotarolimus premounted with a TriMaxx® Coronary Stent.

The coating solution was 0.7 ml ethanol+150 ul Ultravist 370+4.15 ml acetone; thereof 3 ml+135 mg Zotarolimus=45 mg Zotarolimus/ml Zotarolimus. Ethanol content of the solution: 14%. The balloons were coated two times to achieve 13 µl (3.0-17 mm) or 15 µl (3.5-17 mm) by either an automatically adjustable 50 µl or a conventional 25 µl Hamilton syringe. Total consumption/coating step=47×13 µl+59×15 µl+losses=1.5 ml+losses. The drying time between coatings was ≥3 hrs.

TABLE I

Summary of Coating

| Samples | n | µg Zotarolimus | µg/mm² balloon surface | µg/mm balloon length | % of dose |
|---|---|---|---|---|---|
| Unused coated balloons with stents 3.5-17 mm | 5 | 1 200 ± 46 | 6.4 ± 0.2 | 71 ± 3 | 100 |
| Unused coated balloons with stents 3.0-17 mm | 4 | 1073 ± 56 | 6.7 ± 0.3 | 63 ± 3 | 100 |
| Coated balloons after use | 15 | 131 ± 60 | | 7.7 ± 3.5 | 14.1 ± 11.5 |
| Bare balloons with premounted ZoMaxx stents after use | 4 | | not detectable | | |
| Bare balloons with bare stents after use | 3 | | not detectable | | |

The Zotarolimus content of balloons with stents and balloon after stent implantation was calculated and summarized at Table II.

TABLE II

Zotarolimus Content of Balloons With Stents And Balloons After Implantation

| Sample/ Animal no*** | Peak area ABT | Peak area Oxepane | Total area | Conc. ABT µg/ml | ABT-578 µg | % of dose |
|---|---|---|---|---|---|---|
| 25 µg/ml | 722,842 | 43,851 | 766,693 | 25.00 | | |
| 18/3.5-17 | 21 439 952 | 1 620 115 | 23 060 067 | 752 | 1 128 | |
| 31/3.5-17 | 22 734 940 | 1 731 578 | 24 466 518 | 798 | 1 197 | |
| 38/3.5-17 | 23 266 330 | 1 718 515 | 24 984 845 | 815 | 1 222 | |
| 44/3.5-17 | 22 843 718 | 1 669 004 | 24 512 722 | 799 | 1 199 | |
| 54/3.5-17 | 23 859 656 | 1 772 667 | 25 632 323 | 836 | 1 254 | |
| Mean ± SD | | | | | 1 200 ± 46 | |
| 71/3.0-17 | 20 545 884 | 1 629 657 | 22 175 541 | 723 | 1.085 | |
| 72/3.0-17 | 10 559 856 | 1 576 729 | 12 13 585 | 396 | 594 | |
| 88/3.0-17 | 20 479 530 | 1 601 586 | 22 081 116 | 720 | 1.080 | |

TABLE II-continued

Zotarolimus Content of Balloons With Stents And Balloons After Implantation

| Sample/ Animal no*** | Peak area ABT | Peak area Oxepane | Total area | Conc. ABT μg/ml | ABT-578 μg | % of dose |
|---|---|---|---|---|---|---|
| 90/3.0-17 | 18 874 040 | 1 491 887 | 20 365 927 | 664 | 996 | |
| 98/3.0-17 | 21 480 138 | 1 648 244 | 23 128 382 | 754 | 1.131 | |
| Mean ± SD | | | | | 1073 ± 56* | |
| 16**/14 CX | 1 206 986 | 93 207 | 1 300 193 | 42.5 | 63.8 | 5.3 |
| 19/5 CX | 1 186 017 | 101 098 | 1 287 115 | 42.0 | 63.0 | 5.2 |
| 22/43 CX | 2 474 350 | 175 955 | 2 650 305 | 86.7 | 130 | 10.8 |
| 25/20 LAD | 2 266 034 | 159 360 | 2 425 394 | 79.3 | 119 | 9.9 |
| 26/7 CX | 1 129 959 | 71 187 | 1 201 146 | 39.2 | 58.8 | 4.9 |
| 28/2 LAD | 1 817 150 | 143 416 | 1 960 566 | 63.9 | 95.9 | 8.0 |
| 36/32 LAD | 4 119 968 | 300 699 | 4 420.667 | 145 | 217 | 18.1 |
| 37/34-36 LAD | 2 600 973 | 186 731 | 2 787 704 | 91.2 | 137 | 11.4 |
| 43/3 CX | 5 247 028 | 394 311 | 5 641 339 | 184 | 276 | 23.0 |
| 48**/21 CX | 2 621 613 | 195 138 | 2 816 751 | 92.1 | 138 | 11.5 |
| 49/17 LAD | 3 526 794 | 261 929 | 3 788 723 | 124 | 186 | 15.5 |
| 51/19 LAD | 2 996 942 | 221 358 | 3 218 300 | 105 | 158 | 13.2 |
| 53/10 LAD | 2 112 427 | 145 245 | 2 257 672 | 73.8 | 111 | 9.2 |
| 56/24 CX | 2 232 040 | 161 731 | 2 393 771 | 78.3 | 117 | 9.8 |
| 92**/13 CX | 1 828 869 | 135 997 | 1 964 866 | 64.3 | 96.4 | 9.0 |
| **) more blood than on other balloons | | | | | 131 ± 60 | 14.1 ± 11.5 |
| DES/17 | no peak | | | | | |
| DES/23 | no peak | | | | | |
| DES/27 | no peak | | | | | |
| DES/28 | no peak | | | | | |
| No drug/3LAD | no peak | | | | | |
| No drug/19 CX | no peak | | | | | |
| No drug/2CX | no peak | | | | | |

The Zotarolimus measurements were made according to the following method, the gradient clean up was not performed. Zorbax Eclipse XDB-C8 columns sized 4.6×75 mm by 3.5 micrometers, the column temperature of 45 degrees centigrade at a flow rate of 1 ml/min, the flow media 51% ammonia acetate buffer ph 4.9; 49% acetone nitrile, injection volume 20 micro liters, UV detection 278 nm.

Each stent delivery system was prepared by flushing the guidewire lumen with heparinized saline solution. Air was aspirated from the balloon lumen using negative pressure, filling lumen with a 50/50 mixture of 0.9% normal saline and contrast solution. Stents were then introduced into the coronary arteries by advancing the stented balloon catheter through the guide catheter and over the guidewire to the deployment site within the LAD or CX. The balloon was then inflated at a steady rate to a pressure sufficient to target a stent:artery ratio of 1.2. Confirmation of this stent-artery ratio was made when the angiographic images were quantitatively assessed. After the target balloon to artery ratio was achieved for 60 seconds, vacuum was applied to the inflation device in order to deflate the balloon. The delivery system was removed.

Contrast injections were used to determine device patency and additional acute system was noted. This process was repeated until all devices were deployed. All catheters were then removed from the animal and the carotid artery was ligated. At this time, blood pressure monitoring was terminated. The incision was closed in layers with suture materials. The skin was closed with closure materials. The pigs were returned to their cages and allowed to recover from anesthesia. To prevent infection, pigs were given Urocyclin 10% at appropriate dosage levels at least 1 day prior to implantation and on the day of implantation. Additional doses were administered as necessary.

After 28 days, the pigs were sacrificed using pentobarbital in deep anesthesia. Hearts were rapidly excised, the coronary system flushed with 0.9% saline and the arteries fixed by perfusion with 4% buffered formalin under physiological pressure and overnight immersion. The target segments were then dissected and samples for histology obtained.

C. Data Collection

1. Semi-Quantitative and Quantitative Coronary Analysis (QCA)

Coronary imaging was done using a Philips PolyArc fluoroscope connected to a digitizer using an Apple Macintosch Power PC. A semi-quantitative evaluation of coronary angiography was performed with the following grading: 0=no signs of neointimal hyperplasia (identical with result immediately after stent implantation); 1=slight signs of neointimal hyperplasia; 2=moderate signs of neointimal hyperplasia (minimal lumen diameter in-stent identical with vessel reference diameter); 3=clear signs of neointimal hyperplasia (minimal lumen diameter in-stent identical with vessel reference diameter); 4=strong signs of neointimal hyperplasia, about 50% of reference diameter; and 5=distinct signs of neointimal hyperplasia (vessel nearly or totally occluded). The CAAS II for Research System (Pie Medical, the Netherlands) was used for quantitative coronary analysis.

2. Histology

Hearts were rapidly excised, the coronary system flushed with 0.9% saline and the arteries fixed by perfusion with 4% buffered formalin under physiological pressure and overnight immersion. Stented coronary arteries were dissected from the formalin-fixed hearts and immersed in methylmethacrylate (Merck, Darmstadt, Germany). Three representative cross sections per stent were separated from the blocks with a rotation microtome (Leica RM 2255), polished, and glued on acrylic plastic slides. Final specimens were stained by HE and Masson-Goldner technique. After digitalizing, histomorphometric measurements were taken with the NIH image program (PC version 'Scion Image,' Scion Corporation, Maryland, USA). The evaluated parameters were: luminal area, external elastic lamina (EEL) diameter, maximal neointimal thickness, EEL area, luminal area, and neointimal area.

Histomorphometric variables of the three cross-sectional planes were averaged to obtain a mean value per stent. Continuous variables were compared by ANOVA analysis using the software package SPSS 13.0 for Windows (SPSS Inc. Chicago, Ill.). Data are presented as the mean value±SD.

D. Results

1. Semi-quantitative angiographic coronary analysis

Figure 15:
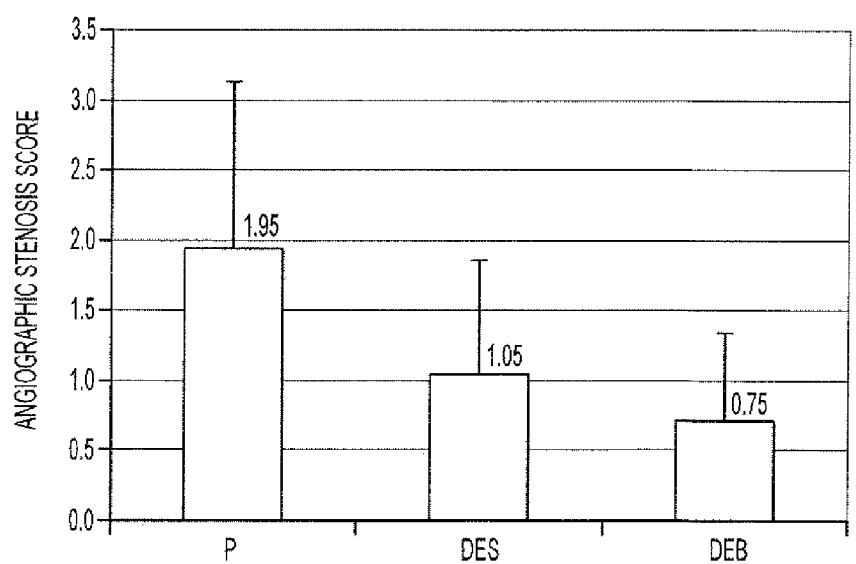
FIG. 15 is a graph illustrating comparative results of Semi-quantitative Angiographic Scoring of P (TriMaxx Stent on uncoated balloon), DEB (TriMaxx Stent on Zotarolimus coated balloon), and DES (ZoMaxx stent on uncoated balloon).

FIG. 15 depicts a graph that illustrates the comparative results of semi-quantitative angiographic scoring (narrowed compared to reference diameter score>1) of P (TriMaxx Stent on uncoated balloon), DEB (TriMaxx Stent on Zotarolimus coated balloon), and DES (ZoMaxx stent on uncoated balloon). An arbitrary scoring system was used in which 0=still oversized, 1=about reference diameter, 2=slightly less than reference diameter, 3=significantly less than reference diameter, 4=very narrow but not included, 5=occluded. As illustrated below in Graph 1, the angiographic stenosis score reveals a reduction of stenosis by the drug eluting stent (DES) and a further improved reduction of stenosis of the Zotarolimus coated balloon (DEB) after one month.

Table III below summarizes the individual results of the semiquantitative angiographic scoring.

TABLE III

Individual Results of Semi-Quantitative Angiographic Scoring

| Animal number | Vessel | | Vessel | |
|---|---|---|---|---|
| #7 | LAD | 3-4 | CX | 0 |
| #8 | LAD | 2 | CX | 2 |
| #9 | LAD | 3-4 | CX | 0-1 |
| #10 died shortly after the intervention | | | | |
| #11 | LAD | 3 | CX | 1 |
| #12 | LAD | 3 | CX | 1 |
| #13 | LAD | 2 | CX | 0 |
| #14 | LAD | 4 | CX occlusion several cm to stent, infarction | |
| #15 | LAD | 4 | CX | 1 |
| #16 | LAD | 0-1 | CX | 1 |
| #17 | LAD | 3 | CX | 2 |
| #18 | LAD | 2-3 | CX | 1 |
| #19 | LAD | 1 | CX | 1 |
| #20 | LAD | 3-4 | CX | 0 |
| #21 | LAD | 4 | CX | 1-2 |
| #22 | LAD | 1 | CX | 3 |
| #23 | LAD | (0)-1 | CX | 1 |
| #24 | LAD | 1 | CX | 1 |
| #25 | LAD | (0)-1 | CX | 2 |
| #26 | LAD | 1 | CX | 1 |
| #27 | LAD | 1(-2) | CX | 0 |
| #28 | LAD | 1 | CX | 1 |
| #29 | LAD | 3 | CX | 0 |
| #30 | LAD | 4 | CX | 0 |
| #31 | LAD | 4 | CX | (0)-1 |
| #32 | LAD | 1 | CX | 2 |
| #33 | LAD | 3(-4) | CX | 3 |
| #34 | LAD | 1-2 | CX | 1 |
| #35 | LAD | 2 | CX | (0)-1 |
| #36 | LAD | 1(-2) | CX | 1 |
| #37 | LAD | 1(-2) | CX | (0)-1 |
| #38 died shortly after the intervention | | | | |
| #39 | LAD | 1-(2) | CX | 1 |
| #40 | LAD | (0)-1 | CX | 0 |
| #41 | LAD | 3-4 | CX | 0-1 |
| #42 | LAD | 1-2 | CX | 0 |
| #43 | LAD | 2-3 | CX | 0-1 |
| #44 | LAD | 1-2 | CX | 3 |
| #45 | LAD | 1-2 | CX | 0 |
| #46 | LAD | 3 | CX | 1 |
| #47 | LAD | 3 | CX | 1 |
| #48 | LAD | 1 | CX | 0-1 |
| #49 | LAD | 1-2 | CX | 1-2 |
| #50 | LAD | 3-4 | CX | 1 |

Individual results of semi quantitative angiographic scoring.

0 = still oversized,

1 = about reference diameter,

2 = slightly less reference diameter, 3 significantly less than reference diameter, 4 = very narrow but not occluded, 5 = occluded. Treatment: Placebo (no drug); DES; DEB.

2. Quantitative Coronary Angiography (QCA)

Figure 16:
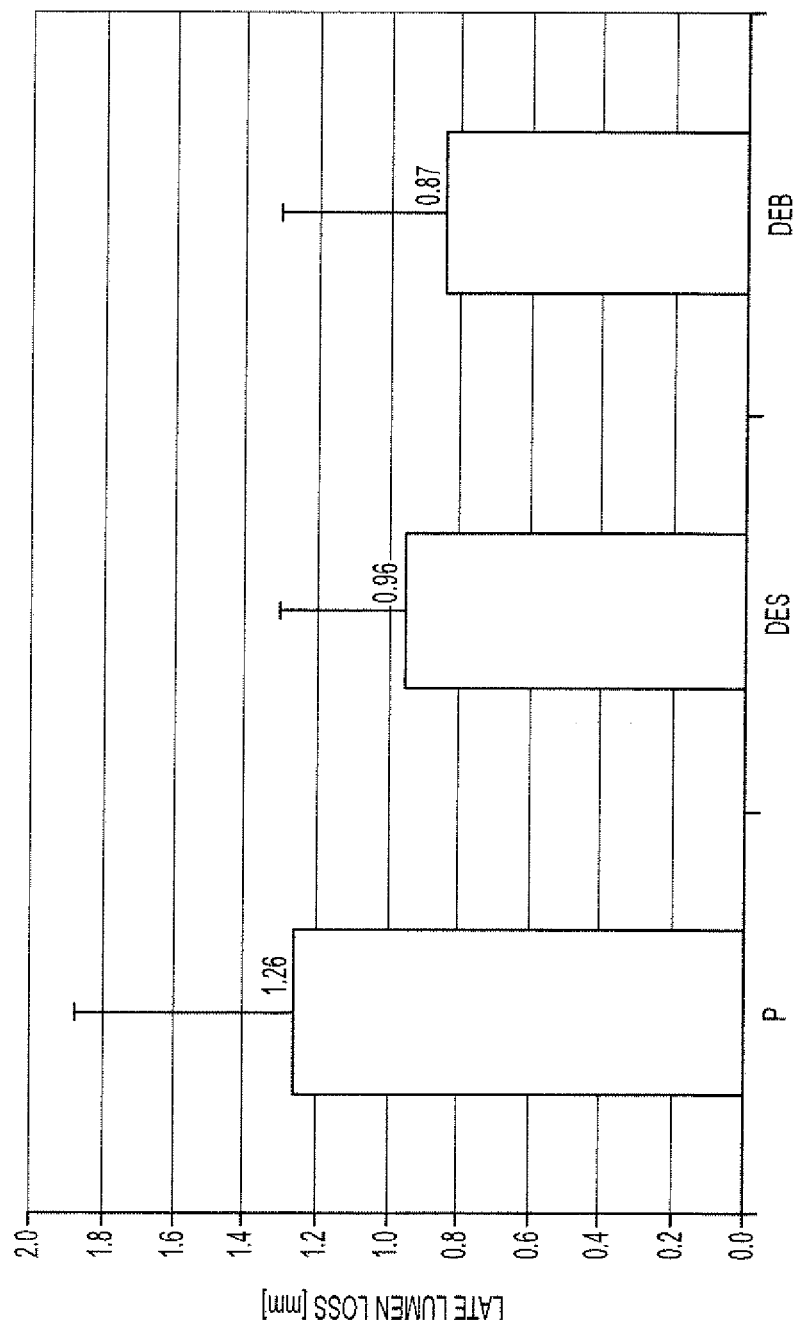
FIG. 16 is a graph illustrating results of Late Lumen Loss of P (TriMaxx Stent on uncoated balloon), DEB (TriMaxx Stent on Zotarolimus coated balloon), and DES (ZoMaxx stent on uncoated balloon) by Quantitative Coronary Angiography.

As illustrated in FIG. 16 and Tables IV, V, and VI below, QCA reveals a reduction of late lumen loss by the Zotarolimus coated stent and the Zotarolimus coated balloon. FIG. 16 depicts a graph that illustrates Summary of Results of Late Lumen Loss [mm] of P (TriMaxx Stent on uncoated balloon), DEB (TriMaxx Stent on Zotarolimus coated balloon), and DES (ZoMaxx stent on uncoated balloon) assessed by QCA.

TABLE IV

Results of QCA

| | P | DES | DEB | p |
|---|---|---|---|---|
| | stent implantation | | | |
| RFD [mm] | 2.30 ± 0.37 | 2.22 ± 0.39 | 2.33 ± 0.33 | 0.688 |
| stent diameter [mm] | 2.69 ± 0.31 | 2.66 ± 0.28 | 2.64 ± 0.26 | 0.826 |
| overstretch [—] | 1.18 ± 0.15 | 1.22 ± 0.17 | 1.14 ± 0.11 | 0.380 |
| | control angiography | | | |
| RFD control [mm] | 2.38 ± 0.27 | 2.31 ± 0.23 | 2.31 ± 0.30 | 0.463 |
| MLD control [mm] | 1.44 ± 0.58 | 1.69 ± 0.45 | 1.77 ± 0.49 | 0.126 |
| late lumen loss [mm] | 1.26 ± 0.61 | 0.96 ± 0.36 | 0.87 ± 0.47 | 0.028 |

RFD = reference diameter at baseline [mm], stent diameter [mm], overstretch ratio [—], RFD at control [mm], MLD minimal lumen diameter at control [mm], and late lumen loss [mm]. ANOVA analysis.

TABLE V p-Values of QCA

| | p P vs DES | p P vs DEB | p DES vs DEB |
|---|---|---|---|
| RFD [mm] | 0.460 | 0.790 | 0.421 |
| stent diameter [mm] | 0.732 | 0.575 | 0.853 |
| overstretch [—] | 0.432 | 0.329 | 0.167 |
| RFD control [mm] | 0.323 | 0.351 | 0.994 |
| MLD control [mm] | 0.125 | 0.122 | 0.978 |
| late lumen loss [mm] | 0.084 | 0.027 | 0.550 |

TABLE VI

Results of QCA for LAD only

| only LAD | P | DES | DEB | p |
|---|---|---|---|---|
| stent implantation | | | | |
| RFD [mm] | 2.17 ± 0.28 | 2.01 ± 0.33 | 2.13 ± 0.19 | 0.409 |
| stent diameter [mm] | 2.59 ± 0.22 | 2.58 ± 0.24 | 2.55 ± 0.24 | 0.898 |
| overstretch [—] | 1.21 ± 0.18 | 1.31 ± 0.21 | 1.20 ± 0.10 | 0.395 |
| control angiography | | | | |
| RFD control [mm] | 2.32 ± 0.24 | 2.15 ± 0.10 | 2.16 ± 0.24 | 0.110 |
| MLD control [mm] | 1.18 ± 0.50 | 1.42 ± 0.38 | 1.42 ± 0.38 | 0.318 |
| late lumen loss [mm] | 1.41 ± 0.61 | 1.15 ± 0.37 | 1.13 ± 0.37 | 0.328 |

TABLE VII

Results of QCA for CX only

| only CX | P | DES | DEB | p |
|---|---|---|---|---|
| stent implantation | | | | |
| RFD [mm] | 2.44 ± 0.40 | 2.43 ± 0.35 | 2.53 ± 0.31 | 0.829 |
| stent diameter [mm] | 2.78 ± 0.36 | 2.73 ± 0.33 | 2.73 ± 0.26 | 0.886 |
| overstretch [—] | 1.15 ± 0.11 | 1.13 ± 0.05 | 1.08 ± 0.09 | 0.242 |
| control angiography | | | | |
| RFD control [mm] | 2.45 ± 0.28 | 2.46 ± 0.23 | 2.46 ± 0.29 | 0.997 |
| MLD control [mm] | 1.69 ± 0.54 | 1.96 ± 0.35 | 2.12 ± 0.29 | 0.235 |
| late lumen loss [mm] | 1.11 ± 0.57 | 0.77 ± 0.22 | 0.60 ± 0.43 | 0.153 |

Tables VIII and IX summarize the individual results of QCA for the animals in the study.

TABLE VIII

Individual QCA Results for animals G59/007-G59/028

| ID | group | RFD | Stent | RFD control | MLD control | overstretch | late loss |
|---|---|---|---|---|---|---|---|
| G59007cx | P | 2.42 | 2.71 | 2.41 | 1.68 | 1.12 | 1.03 |
| G59007lad | P | 2.31 | 2.58 | 2.20 | 0.82 | 1.12 | 1.76 |
| G59008cx | P | 2.14 | 2.62 | 2.28 | 1.50 | 1.22 | 1.12 |
| G59008lad | DEB | 2.13 | 2.54 | 1.99 | 1.26 | 1.19 | 1.28 |
| G59009cx | DEB | 2.30 | 2.78 | 2.21 | 2.35 | 1.21 | 0.43 |
| G59009lad | P | 1.94 | 2.42 | 2.16 | 0.98 | 1.25 | 1.44 |
| G59010cx | P | | | | | | |
| G59010lad | P | | | | | | |
| G59011cx | DEB | 2.63 | 2.89 | 2.22 | 2.25 | 1.10 | 0.64 |
| G59011lad | P | 2.19 | 2.61 | 1.78 | 0.85 | 1.19 | 1.76 |
| G59012cx | P | 2.80 | 3.22 | 2.63 | 1.88 | 1.15 | 1.34 |
| G59012lad | P | 2.52 | 2.78 | 2.67 | 0.86 | 1.10 | 1.92 |
| G59013cx | DEB | 2.59 | 2.76 | 2.59 | 1.57 | 1.07 | 1.19 |
| G59013lad | P | 2.24 | 2.66 | 2.39 | 1.42 | 1.19 | 1.24 |
| G59014cx | P | 2.53 | 2.93 | 2.53 | 0.01 | 1.16 | 2.92 |
| G59014lad | P | 1.91 | 2.58 | 2.54 | 0.84 | 1.35 | 1.74 |
| G59015cx | P | 2.40 | 2.91 | 2.31 | 1.84 | 1.21 | 1.07 |
| G59015lad | P | 1.84 | 2.91 | 1.73 | 0.20 | 1.58 | 2.71 |
| G59016cx | P | 3.07 | 3.18 | 3.11 | 2.20 | 1.04 | 0.98 |
| G59016lad | DEB | 2.42 | 2.73 | 2.29 | 1.71 | 1.13 | 1.02 |
| G59017cx | P | 1.92 | 2.72 | 1.99 | 1.09 | 1.42 | 1.63 |
| G59017lad | P | 2.57 | 2.69 | 2.45 | 1.59 | 1.05 | 1.10 |
| G59018cx | P | 2.39 | 2.52 | 2.60 | 1.95 | 1.05 | 0.57 |
| G59018lad | P | 2.23 | 2.53 | 2.46 | 1.27 | 1.13 | 1.26 |
| G59019cx | DEB | 2.51 | 2.89 | 2.65 | 2.31 | 1.15 | 0.58 |
| G59019lad | P | 2.39 | 2.68 | 2.21 | 1.22 | 1.12 | 1.46 |
| G59020cx | DEB | 2.47 | 2.70 | 2.35 | 1.99 | 1.09 | 0.71 |
| G59020lad | P | 2.12 | 2.51 | 2.16 | 1.08 | 1.18 | 1.43 |
| G59021cx | P | 2.48 | 2.48 | 2.74 | 1.56 | 1.00 | 0.92 |
| G59021lad | P | 2.25 | 2.41 | 2.51 | 1.15 | 1.07 | 1.26 |
| G59022cx | P | 2.00 | 2.38 | 2.04 | 1.08 | 1.19 | 1.30 |
| G59022lad | P | 2.30 | 2.56 | 2.48 | 1.99 | 1.11 | 0.57 |
| G59023cx | P | 2.59 | 2.87 | 2.42 | 1.62 | 1.11 | 1.25 |
| G59023lad | DEB | 1.79 | 2.23 | 2.13 | 1.08 | 1.25 | 1.15 |
| G59024cx | P | 2.76 | 2.92 | 2.64 | 2.68 | 1.06 | 0.24 |
| G59024lad | P | 2.47 | 2.62 | 2.45 | 2.28 | 1.06 | 0.34 |
| G59025cx | P | 1.85 | 2.18 | 2.13 | 1.38 | 1.18 | 0.80 |
| G59025lad | DEB | 2.11 | 2.35 | 2.50 | 1.89 | 1.11 | 0.46 |
| G59026cx | P | 2.72 | 2.93 | 2.76 | 2.18 | 1.08 | 0.75 |
| G59026lad | DEB | 2.05 | 2.82 | 2.24 | 1.83 | 1.38 | 0.99 |
| G59027cx | DEB | 2.11 | 2.16 | 2.97 | 2.36 | 1.02 | −0.20 |
| G59027lad | P | 2.26 | 2.48 | 2.30 | 1.90 | 1.10 | 0.58 |
| G59028cx | P | 2.22 | 2.54 | 2.35 | 1.18 | 1.14 | 1.36 |
| G59028lad | DES | 2.09 | 2.32 | 2.24 | 1.33 | 1.11 | 0.99 |

TABLE IX

Individual QCA Results for animals G59/029-G59/050

| ID | group | RFD Stent | RFD control | MLD control | overstretch |
|---|---|---|---|---|---|
| G59029cx | DES | 2.16 2.53 | 2.34 | 1.71 | 1.17 |
| G59029lad | P | 1.50 2.55 | 2.33 | 1.18 | 1.70 |
| G59030cx | DEB | 3.12 2.90 | 2.21 | 2.02 | 0.93 |
| G59030lad | P | 2.57 2.40 | 2.56 | 0.69 | 0.93 |
| G59031cx | DES | 2.72 2.82 | 2.94 | 2.35 | 1.04 |
| G59031lad | P | 2.10 2.73 | 2.39 | 0.89 | 1.30 |
| G59032cx | P | 2.53 2.61 | 2.69 | 0.83 | 1.03 |
| G59032lad | P | 1.97 2.36 | 2.65 | 2.05 | 1.20 |
| G59033cx | P | 1.85 2.15 | 2.05 | 1.38 | 1.16 |
| G59033lad | DES | 1.76 2.40 | 2.01 | 0.67 | 1.36 |
| G59034cx | P | 2.12 2.29 | 2.18 | 1.74 | 1.08 |
| G59034lad | DES | 2.15 2.45 | 2.22 | 1.87 | 1.14 |
| G59035cx | P | 2.63 2.84 | 2.72 | 2.36 | 1.08 |
| G59035lad | DES | 2.43 2.71 | 2.30 | 1.35 | 1.12 |
| G59036cx | P | 1.97 2.44 | 2.24 | 2.24 | 1.24 |
| G59036lad | P | 2.03 2.23 | 2.57 | 1.70 | 1.10 |
| G59037cx | P | 2.57 3.33 | 2.84 | 2.26 | 1.30 |
| G59037lad | P | 2.36 2.66 | 2.36 | 1.77 | 1.13 |
| G59038cx | P | | | | |
| G59038lad | DEB | | | | |
| G59039cx | DES | 2.00 2.32 | 2.38 | 1.45 | 1.16 |
| G59039lad | P | 2.18 2.60 | 2.08 | 1.12 | 1.19 |
| G59040cx | P | 3.06 3.16 | 2.59 | 2.09 | 1.03 |
| G59040lad | DES | 1.95 2.77 | 2.09 | 1.64 | 1.42 |
| G59041cx | DES | 3.03 3.33 | 2.32 | 2.21 | 1.10 |
| G59041lad | P | 2.71 3.20 | 2.34 | 1.16 | 1.18 |
| G59042cx | P | 2.42 2.64 | 2.55 | 1.98 | 1.09 |
| G59042lad | DEB | 2.24 2.80 | 2.22 | 1.16 | 1.25 |
| G59043cx | DES | 2.25 2.53 | 2.54 | 1.63 | 1.12 |
| G59043lad | P | 2.51 2.74 | 2.45 | 0.36 | 1.09 |
| G59044cx | P | 3.59 3.65 | 2.72 | 1.57 | 1.02 |
| G59044lad | DES | 2.27 2.96 | 2.15 | 1.58 | 1.30 |
| G59045cx | DES | 2.52 2.87 | 2.37 | 2.21 | 1.14 |
| G59045lad | P | 1.97 2.39 | 2.16 | 1.23 | 1.21 |
| G59046cx | DES | 2.33 2.72 | 2.32 | 2.17 | 1.17 |
| G59046lad | P | 1.99 2.38 | 2.42 | 0.89 | 1.20 |
| G59047cx | P | 2.67 3.03 | 2.37 | 1.67 | 1.13 |
| G59047lad | P | 1.91 2.38 | 2.24 | 1.04 | 1.25 |
| G59048cx | P | 2.22 2.76 | 2.40 | 1.97 | 1.24 |
| G59048lad | DES | 1.45 2.44 | 2.07 | 1.53 | 1.68 |
| G59049cx | P | 2.01 2.80 | 2.23 | 1.61 | 1.39 |
| G59049lad | DEB | 2.20 2.35 | 1.73 | 0.99 | 1.07 |
| G59050cx | P | 2.60 3.39 | 2.12 | 1.72 | 1.30 |
| G59050lad | P | 1.82 3.08 | 1.83 | 0.64 | 1.69 |

3. Histomorphometry

As represented in Tables X, XI, XII, and XIII, histomorphometry revealed a significant reduction of neointimal formation by the Zotarolimus coated balloon and Zotarolimus coated stent. FIG. 17 is a graph illustrating results of Neointimal Area [mm] by histomorphometry of P (TriMaxx Stent on uncoated balloon), DEB (TriMaxx Stent on Zotarolimus coated balloon), and DES (ZoMaxx stent on uncoated balloon).

TABLE X

Results of Histomorphometry

| | P | DES | DEB | p |
|---|---|---|---|---|
| n | 56 | 14 | 14 | all |
| vessel diameter [mm] | 3.07 ± 0.16 | 2.94 ± 0.17 | 3.07 ± 0.16 | 0.041 |
| lumen diameter [mm] | 1.93 ± 0.48 | 2.15 ± 0.35 | 2.20 ± 0.37 | 0.059 |
| max. neoint. thickn. [mm] | 0.63 ± 0.37 | 0.38 ± 0.21 | 0.49 ± 0.46 | 0.055 |
| vessel area [mm$^2$] | 7.44 ± 0.79 | 7.05 ± 0.49 | 7.17 ± 1.08 | 0.196 |
| luminal area [mm$^2$] | 3.12 ± 1.25 | 3.73 ± 0.98 | 4.38 ± 1.37 | 0.003 |
| neointimal area [mm$^2$] | 4.32 ± 1.45 | 3.32 ± 1.11 | 2.79 ± 1.43 | 0.001 |
| area stenosis [%] | 58% ± 17% | 47% ± 13% | 38% ± 19% | 0.001 |
| injury score [—] | 1.20 ± 0.86 | 1.25 ± 0.92 | 1.16 ± 0.43 | 0.961 |
| inflammation score [—] | 1.45 ± 0.94 | 1.65 ± 0.90 | 0.75 ± 0.86 | 0.021 |

Vessel diameter [mm], lumen diameter [mm], maximal neointimal thickness [mm], vessel area [mm$^2$], area stenosis [%], injury score [—], and inflammation score [—]. ANOVA analysis.

TABLE XI

Comparison of p-Values of Histomorphometry

| n | p P vs DES | p P vs DEB | p DES vs DEB |
|---|---|---|---|
| vessel diameter [mm] | 0.015 | 0.943 | 0.054 |
| lumen diameter [mm] | 0.109 | 0.052 | 0.717 |
| max. neoint. thickn. [mm] | 0.018 | 0.213 | 0.453 |
| vessel area [mm$^2$] | 0.083 | 0.286 | 0.715 |
| luminal area [mm$^2$] | 0.096 | 0.002 | 0.161 |
| neointimal area [mm$^2$] | 0.019 | 0.001 | 0.281 |
| area stenosis [%] | 0.028 | 0.001 | 0.186 |
| injury score [—] | 0.844 | 0.885 | 0.752 |
| inflammation score [—] | 0.482 | 0.013 | 0.012 |

TABLE XII

Results of Histomorphometry for CX only

| only CX | P | DES | DEB | p |
|---|---|---|---|---|
| n | 28 | 7 | 7 | |
| vessel diameter [mm] | 3.01 ± 0.17 | 2.85 ± 0.20 | 3.01 ± 0.17 | 0.109 |
| lumen diameter [mm] | 1.93 ± 0.53 | 2.17 ± 0.17 | 2.23 ± 0.50 | 0.426 |
| max. neoint. thickn. [mm] | 0.53 ± 0.32 | 0.34 ± 0.11 | 0.33 ± 0.29 | 0.254 |
| vessel area [mm$^2$] | 7.16 ± 0.85 | 6.74 ± 0.42 | 6.96 ± 1.14 | 0.489 |
| luminal area [mm$^2$] | 3.33 ± 1.32 | 3.74 ± 0.50 | 4.24 ± 1.71 | 0.246 |
| neointimal area [mm$^2$] | 3.83 ± 1.38 | 3.00 ± 0.55 | 2.72 ± 1.56 | 0.087 |
| area stenosis [%] | 53% ± 17% | 44% ± 7% | 39% ± 22% | 0.106 |
| injury score [—] | 1.23 ± 0.91 | 1.14 ± 0.66 | 1.19 ± 0.23 | 0.963 |
| inflammation score [—] | 1.48 ± 1.06 | 1.57 ± 0.63 | 0.71 ± 0.81 | 0.157 |

TABLE XIII

Results of Histomorphometry for LAD only

| only LAD | P | DES | DEB | p |
|---|---|---|---|---|
| n | 28 | 7 | 7 | |
| vessel diameter [mm] | 3.12 ± 0.14 | 3.03 ± 0.07 | 3.13 ± 0.14 | 0.258 |
| lumen diameter [mm] | 1.93 ± 0.41 | 2.13 ± 0.48 | 2.17 ± 0.22 | 0.110 |
| max. neoint. thickn. [mm] | 0.73 ± 0.39 | 0.43 ± 0.29 | 0.64 ± 0.57 | 0.221 |
| vessel area [mm$^2$] | 7.73 ± 0.62 | 7.36 ± 0.32 | 7.38 ± 1.06 | 0.285 |
| luminal area [mm$^2$] | 2.91 ± 1.17 | 3.72 ± 1.35 | 4.52 ± 1.06 | 0.007 |
| neointimal area [mm$^2$] | 4.82 ± 1.37 | 3.65 ± 1.46 | 2.86 ± 1.41 | 0.004 |
| area stenosis [%] | 62% ± 15% | 49% ± 18% | 38% ± 18% | 0.002 |
| injury score [—] | 1.16 ± 0.83 | 1.36 ± 1.17 | 1.14 ± 0.59 | 0.856 |
| inflammation score [—] | 1.43 ± 0.31 | 1.73 ± 1.16 | 0.79 ± 0.98 | 0.139 |

Tables XIV and XV summarize the individual results of histomorphometry.

TABLE XIV

Individual Results of Histomorphometry for animals G59/007-G59/028

| ID | group | vesdia | lumdia | max thick | vesarea | lumarea | neoint | area stenosis | injury | inflammation |
|---|---|---|---|---|---|---|---|---|---|---|
| G59007cx | P | 3.10 | 2.33 | 0.40 | 7.70 | 4.29 | 3.41 | 44.3% | 0.50 | 0.44 |
| G59007lad | P | 3.17 | 1.39 | 1.09 | 7.89 | 1.53 | 6.36 | 80.6% | 0.20 | 0.22 |
| G59008cx | P | 3.02 | 1.93 | 0.66 | 7.19 | 2.89 | 4.30 | 59.9% | 0.90 | 0.22 |
| G59008lad | DEB | 3.32 | 1.91 | 0.63 | 8.56 | 4.75 | 3.81 | 44.5% | 0.86 | 1.33 |
| G59009cx | DEB | 3.04 | 2.32 | 0.48 | 7.26 | 3.28 | 3.98 | 54.8% | 0.90 | 0.44 |
| G59009lad | P | 3.32 | 2.40 | 0.38 | 8.59 | 4.55 | 4.04 | 47.1% | 0.20 | 0.44 |
| G59010cx | P | | | | | | | | | |
| G59010lad | P | | | | | | | | | |
| G59011cx | DEB | 2.98 | 1.15 | 0.93 | 6.92 | 1.33 | 5.59 | 80.8% | 1.29 | 1.00 |
| G59011lad | P | 3.09 | 2.14 | 0.38 | 6.99 | 3.34 | 3.65 | 52.3% | 0.10 | 0.56 |
| G59012cx | P | 3.21 | 2.02 | 0.66 | 7.92 | 3.24 | 4.68 | 59.1% | 1.00 | 0.44 |
| G59012lad | P | 3.19 | 1.48 | 0.96 | 7.93 | 1.84 | 6.10 | 76.8% | 2.00 | 2.33 |
| G59013cx | DEB | 3.11 | 2.52 | 0.14 | 7.57 | 5.57 | 2.00 | 26.4% | 1.11 | 0.22 |
| G59013lad | P | 3.14 | 1.94 | 0.68 | 7.59 | 2.97 | 4.63 | 60.9% | 1.30 | 1.56 |
| G59014cx | P | 3.12 | 0.01 | 1.50 | 7.44 | 0.01 | 7.43 | 99.9% | 3.00 | 3.00 |
| G59014lad | P | 3.41 | 1.33 | 1.61 | 9.65 | 1.31 | 8.35 | 86.5% | 3.00 | 3.00 |
| G59015cx | P | 3.07 | 1.89 | 0.73 | 7.59 | 2.84 | 4.74 | 62.5% | 1.30 | 1.00 |
| G59015lad | P | 3.16 | 0.75 | 1.99 | 8.07 | 0.44 | 7.64 | 94.6% | 1.80 | 2.44 |
| G59016cx | P | 3.28 | 2.45 | 0.30 | 8.30 | 4.74 | 3.56 | 42.9% | 0.10 | 0.22 |
| G59016lad | DEB | 3.25 | 2.28 | 0.35 | 8.13 | 4.41 | 3.72 | 45.8% | 0.40 | 0.44 |
| G59017cx | P | 2.78 | 1.16 | 0.88 | 5.96 | 1.04 | 1.92 | 82.6% | 1.90 | 1.56 |
| G59017lad | P | 3.15 | 1.74 | 0.71 | 7.75 | 2.47 | 5.28 | 68.1% | 0.80 | 0.78 |
| G59018cx | P | 2.86 | 2.12 | 0.31 | 6.10 | 3.37 | 2.73 | 44.8% | 0.40 | 0.44 |
| G59018lad | P | 2.78 | 1.84 | 0.71 | 7.45 | 2.71 | 4.74 | 63.6% | 1.20 | 1.11 |
| G59019cx | DEB | 2.66 | 2.21 | 0.17 | 4.51 | 3.46 | 1.06 | 23.4% | 1.00 | 0.22 |
| G59019lad | P | 3.22 | 1.94 | 0.77 | 8.01 | 2.94 | 5.07 | 63.3% | 0.70 | 0.89 |
| G59020cx | DEB | 3.01 | 2.28 | 0.27 | 6.87 | 4.15 | 2.72 | 39.5% | 1.11 | 0.22 |
| G59020lad | P | 3.19 | 2.03 | 0.65 | 8.27 | 3.36 | 4.91 | 59.4% | 0.60 | 0.78 |
| G59021cx | P | 2.85 | 1.96 | 0.47 | 6.33 | 3.10 | 3.23 | 51.7% | 0.80 | 0.44 |
| G59021lad | P | 3.01 | 1.79 | 0.61 | 7.19 | 2.72 | 4.47 | 62.2% | 0.60 | 0.67 |
| G59022cx | P | 2.61 | 1.64 | 0.48 | 5.30 | 2.29 | 3.01 | 56.9% | 1.10 | 0.78 |
| G59022lad | P | 3.01 | 2.13 | 0.46 | 7.02 | 3.43 | 3.59 | 51.2% | 0.50 | 0.78 |
| G59023cx | P | 3.11 | 1.78 | 0.67 | 7.48 | 2.54 | 4.95 | 66.1% | 1.00 | 1.00 |
| G59023lad | DEB | 3.09 | 2.07 | 0.49 | 7.65 | 3.43 | 4.22 | 55.2% | 1.10 | 0.44 |
| G59024cx | P | 2.97 | 2.43 | 0.15 | 6.45 | 4.35 | 2.10 | 32.6% | 0.10 | 0.11 |
| G59024lad | P | 3.22 | 2.67 | 0.13 | 8.05 | 5.71 | 2.34 | 29.0% | 0.40 | 0.00 |
| G59025cx | P | 3.14 | 1.65 | 1.12 | 7.97 | 2.21 | 5.76 | 72.3% | 1.50 | 1.22 |
| G59025lad | DEB | 3.15 | 2.20 | 0.53 | 7.77 | 5.39 | 2.38 | 30.6% | 0.50 | 0.22 |
| G59026cx | P | 3.12 | 2.41 | 0.24 | 7.63 | 4.79 | 2.84 | 37.2% | 0.00 | 0.00 |
| G59026lad | DEB | 3.07 | 2.52 | 0.16 | 7.62 | 5.68 | 1.93 | 25.4% | 1.00 | 0.00 |
| G59027cx | DEB | 3.14 | 2.60 | 0.13 | 7.71 | 5.92 | 1.79 | 23.2% | 0.75 | 0.33 |
| G59027lad | P | 3.27 | 2.10 | 0.55 | 8.28 | 3.65 | 4.62 | 55.9% | 0.80 | 0.89 |
| G59028cx | P | 2.75 | 1.84 | 0.36 | 5.79 | 2.77 | 3.01 | 52.1% | 1.60 | 1.44 |
| G59028lad | DES | 2.98 | 2.40 | 0.24 | 7.10 | 4.48 | 2.63 | 37.0% | 0.20 | 0.22 |

TABLE XV

Individual Results of Histomorphometry for animals G59/029-G59/050

| ID | group | vesdia | lumdia | max thick | vesarea | lumarea | neoint | area stenosis | injury | inflammation |
|---|---|---|---|---|---|---|---|---|---|---|
| G59029cx | DES | 2.93 | 2.01 | 0.41 | 6.78 | 3.29 | 3.49 | 51.4% | 0.70 | 0.89 |
| G59029lad | P | 2.93 | 1.71 | 0.71 | 6.67 | 2.27 | 4.40 | 66.0% | 1.70 | 1.11 |
| G59030cx | DEB | 3.19 | 2.51 | 0.22 | 7.87 | 5.95 | 1.92 | 24.4% | 0.80 | 2.44 |
| G59030lad | P | 3.12 | 1.60 | 0.90 | 7.68 | 2.17 | 5.51 | 71.8% | 0.90 | 1.00 |
| G59031cx | DES | 3.03 | 2.46 | 0.19 | 7.28 | 4.66 | 2.62 | 36.0% | 0.60 | 2.22 |
| G59031lad | P | 3.14 | 1.52 | 0.98 | 7.46 | 2.00 | 5.46 | 73.2% | 2.70 | 2.78 |
| G59032cx | P | 2.69 | 1.72 | 0.58 | 5.99 | 2.34 | 3.65 | 60.9% | 2.80 | 2.56 |
| G59032lad | P | 3.10 | 2.40 | 0.44 | 7.73 | 4.52 | 3.22 | 41.6% | 0.20 | 2.67 |
| G59033cx | P | 3.19 | 1.79 | 0.92 | 8.41 | 2.65 | 5.76 | 68.5% | 3.00 | 3.00 |
| G59033lad | DES | 3.10 | 1.16 | 1.02 | 7.84 | 1.11 | 6.73 | 85.9% | 3.00 | 3.00 |
| G59034cx | P | 2.83 | 2.19 | 0.25 | 6.19 | 3.67 | 2.53 | 40.8% | 0.40 | 2.78 |
| G59034lad | DES | 3.04 | 2.37 | 0.24 | 7.30 | 4.36 | 2.95 | 40.3% | 1.20 | 2.56 |
| G59035cx | P | 3.09 | 2.58 | 0.25 | 7.61 | 5.73 | 1.89 | 27.8% | 1.20 | 1.78 |
| G59035lad | DES | 3.07 | 2.37 | 0.38 | 7.54 | 4.33 | 3.20 | 42.5% | 1.00 | 1.67 |
| G59036cx | P | 3.16 | 2.39 | 0.48 | 7.95 | 4.65 | 3.30 | 41.5% | 1.00 | 1.44 |
| G59036lad | P | 3.01 | 2.38 | 0.38 | 7.19 | 4.39 | 2.80 | 39.0% | 0.50 | 1.22 |
| G59037cx | P | 3.17 | 2.73 | 0.23 | 7.76 | 5.59 | 2.17 | 28.0% | 0.10 | 1.00 |
| G59037lad | P | 3.08 | 2.32 | 0.35 | 7.54 | 4.26 | 3.28 | 43.5% | 0.70 | 1.11 |
| G59038cx | P | | | | | | | | | |
| G59038lad | DEB | | | | | | | | | |

TABLE XV-continued

Individual Results of Histomorphometry for animals G59/029-G59/050

| ID | group | vesdia | lumdia | max thick | vesarea | lumarea | neoint | area stenosis | injury | inflammation |
|---|---|---|---|---|---|---|---|---|---|---|
| G59039cx | DES | 2.89 | 2.05 | 0.48 | 6.55 | 3.26 | 3.28 | 50.2% | 1.90 | 1.00 |
| G59039lad | P | 3.13 | 2.10 | 0.61 | 7.80 | 3.43 | 4.36 | 56.0% | 1.30 | 2.00 |
| G59040cx | P | 3.03 | 2.18 | 0.32 | 7.25 | 3.74 | 3.51 | 48.4% | 1.70 | 1.22 |
| G59040lad | DES | 3.12 | 2.61 | 0.17 | 7.66 | 5.23 | 2.43 | 31.7% | 0.50 | 0.33 |
| G59041cx | DES | 2.84 | 2.26 | 0.22 | 6.49 | 4.05 | 2.45 | 37.7% | 0.70 | 1.22 |
| G59041lad | P | 3.27 | 2.05 | 0.61 | 8.38 | 3.59 | 4.79 | 57.1% | 1.70 | 2.33 |
| G59042cx | P | 2.84 | 2.29 | 0.25 | 6.23 | 3.96 | 2.27 | 36.4% | 0.90 | 4.00 |
| G59042lad | DEB | 3.14 | 2.29 | 1.88 | 5.47 | 5.18 | 0.29 | 5.2% | 0.80 | 0.33 |
| G59043cx | DES | 2.42 | 2.16 | 0.27 | 6.02 | 3.74 | 2.28 | 37.9% | 1.20 | 1.44 |
| G59043lad | P | 3.00 | 2.03 | 0.41 | 7.12 | 3.48 | 3.65 | 51.2% | 1.00 | 1.78 |
| G59044cx | P | 3.04 | 1.65 | 0.80 | 7.68 | 2.12 | 5.55 | 72.3% | 3.00 | 3.00 |
| G59044lad | DES | 2.96 | 2.00 | 0.44 | 7.02 | 3.31 | 3.71 | 52.9% | 3.00 | 3.00 |
| G59045cx | DES | 2.96 | 2.24 | 0.35 | 6.97 | 3.82 | 3.15 | 45.2% | 1.80 | 1.56 |
| G59045lad | P | 3.01 | 1.97 | 0.55 | 7.34 | 3.12 | 4.22 | 57.5% | 1.50 | 1.56 |
| G59046cx | DES | 2.91 | 1.98 | 0.44 | 7.09 | 3.36 | 3.73 | 52.6% | 1.90 | 2.44 |
| G59046lad | P | 2.96 | 1.50 | 1.00 | 7.09 | 1.83 | 5.27 | 74.2% | 1.90 | 1.44 |
| G59047cx | P | 2.98 | 2.21 | 0.36 | 7.21 | 3.78 | 3.43 | 47.5% | 2.00 | 1.78 |
| G59047lad | P | 2.98 | 1.56 | 0.79 | 7.20 | 1.90 | 5.30 | 73.6% | 1.80 | 1.22 |
| G59048cx | P | 3.10 | 2.63 | 0.14 | 7.61 | 5.15 | 2.46 | 32.3% | 0.60 | 1.00 |
| G59048lad | DES | 2.96 | 2.01 | 0.50 | 7.08 | 3.21 | 3.87 | 54.7% | 0.80 | 1.22 |
| G59049cx | P | 3.15 | 1.75 | 0.83 | 7.99 | 2.45 | 5.54 | 69.3% | 1.60 | 2.00 |
| G59049lad | DEB | 2.87 | 1.90 | 0.44 | 6.46 | 2.80 | 3.66 | 56.7% | 2.30 | 2.78 |
| G59050cx | P | 3.11 | 1.99 | 0.58 | 7.46 | 2.94 | 4.51 | 60.5% | 1.70 | 2.22 |
| G59050lad | P | 3.35 | 1.41 | 1.12 | 8.45 | 1.63 | 6.82 | 80.7% | 2.90 | 2.44 |

4. Conclusion:

The studies indicate show a significant reduction of neointimal formation by the Zotarolimus coated stent and coated balloon. The efficacy in reduction of neointimal formation by the Zotarolimus coated balloon is comparable to the Zotarolimus coated stent, and in some instances the zotarolimus coated balloon has greater efficacy than the zotarolimus coated stent.

The methods and systems of the present invention, as described above and shown in the drawings, provide for a balloon catheter with superior properties including superior therapeutic agent delivery and post-deployment catheter withdrawal capabilities. It will be apparent to those skilled in the art that various modifications and variations can be made in the device and method of the present invention without departing from the spirit or scope of the invention. For example, the instant invention can work particularly well to treat dialysis grafts. As is well known in the art, dialysis grafts are essentially sheaths connecting the arterial and venous sides of a patient's vasculature as is required when a patient is on dialysis for kidney failure. As these sheaths have a tendency for rapid and substantial restenosis, the above-described embodiments would be advantageous as an anti-restenoic agent could be delivered to the graft and the delivery would be less traumatic and more easily adjusted to fit the anatomy of the grafts. Thus, it is intended that the present invention include modifications and variations that are within the scope of the appended claims and their equivalents.

What is claimed is:

1. A balloon catheter comprising:
   an inner shaft member having a proximal end portion, a distal end portion, and a length therebetween, the inner shaft member defining a guidewire lumen therein, the guidewire lumen having a distal port;
   an outer shaft member movable relative to the inner shaft member between an initial delivery condition and a deployed condition, the distal port of the guidewire lumen being exposed to an environment external to the outer shaft member when the inner shaft member is in the initial delivery condition relative the outer shaft member, the outer shaft member having a proximal end portion, a distal end portion, and a length therebetween;
   an annular flow passage disposed between the inner and outer shaft members;
   a flexible membrane attached to and extending between the distal end portion of the inner shaft member and the distal end portion of the outer shaft member; and
   wherein the flexible membrane includes an inner surface and an outer surface, the inner surface configured in fluid communication with the annular flow passage, and further wherein the outer shaft member and the inner shaft member define a chamber in the initial delivery condition configured to receive the flexible membrane rolled in a generally axial direction therein.

2. The balloon catheter of claim 1 wherein the outer shaft member is axially movable relative to the inner shaft member.

3. The balloon catheter of claim 2 including a dynamic seal disposed between the inner shaft member and the outer shaft member to maintain a sealed environment of the annular flow passage during movement of the outer shaft relative to the inner shaft.

4. The balloon catheter of claim 1 wherein the outer surface of the flexible membrane is attached to the inner surface of the outer shaft member and the outer surface of the flexible membrane is attached to the outer surface of the inner shaft member.

5. The balloon catheter of claim 1 wherein the outer shaft member is rotatably movable relative to the inner shaft member.

6. The balloon catheter of claim 5 including a dynamic seal disposed between the inner shaft member and the outer shaft member to maintain a sealed environment of the annular flow passage during movement of the outer shaft relative to the inner shaft.

7. The balloon catheter of claim 1 including a retrieval element attached to the inner shaft member.

8. A method of treating a luminal system of a patient comprising:
  providing a balloon catheter including:
    an inner shaft member having a proximal end portion, a distal end portion, and a length therebetween, the inner shaft member defining a guidewire lumen therein, the guidewire lumen having a distal port;
    an outer shaft member movable relative to the inner shaft member between an initial delivery condition and a deployed condition, the outer shaft member having a proximal end portion, a distal end portion, and a length therebetween, with an annular flow passage disposed between the inner and outer shaft members, the distal port of the guidewire lumen being exposed to an environment external to the outer shaft member when the inner shaft member is in the initial delivery condition relative the outer shaft member;
    a flexible membrane extending between the distal end portion of the inner shaft member and the distal end portion of the outer shaft member, the flexible membrane having an inner surface and an outer surface with the inner surface in fluid communication with the annular flow passage, and further wherein the outer shaft member and the inner shaft member define a chamber in the initial delivery condition configured to receive the flexible membrane rolled in a generally axial direction therein;
  positioning the balloon catheter at a desired deployment site;
  moving the outer shaft member relative to the inner shaft member; and
  introducing inflation fluid into the annular flow passage, simultaneously or sequentially with said relative movement, to deploy the flexible membrane into an expanded configuration to treat the luminal system of a patient.

9. The method of claim 8 wherein initial deployment of the flexible membrane at least partially occludes the luminal system of the patient prior to full expansion of the flexible membrane.

10. A balloon catheter comprising:
  an inner shaft member having a proximal end portion, a distal end portion, and a length therebetween, the inner shaft member defining a guidewire lumen therein, the guidewire lumen having a distal port;
  an outer shaft member movable relative to the inner shaft member between an initial delivery condition and a deployed condition, the distal port of the guidewire lumen being exposed to an environment external to the outer shaft member when the inner shaft member is in the initial delivery condition relative the outer shaft member, the outer shaft member having a proximal end portion, a distal end portion, and a length therebetween;
  an annular flow passage disposed between the inner and outer shaft members;
  a flexible membrane attached to and extending between the distal end portion of the inner shaft member and the distal end portion of the outer shaft member; and
  wherein the flexible membrane includes an inner surface and an outer surface, the flexible membrane being free of perforations therethrough, the inner surface configured in fluid communication with the annular flow passage, and further wherein the outer shaft member and the inner shaft member define a chamber in the initial delivery condition configured to receive the flexible membrane rolled in a generally axial direction therein.

11. The balloon catheter of claim 10 wherein the flexible membrane includes a therapeutic agent disposed on the outer surface thereof.

12. The balloon catheter of claim 1 wherein the flexible membrane includes a therapeutic agent disposed on the outer surface thereof when the inner shaft member is in the initial delivery condition.

* * * * *